United States Patent
Hainfeld

(10) Patent No.: US 10,918,742 B2
(45) Date of Patent: Feb. 16, 2021

(54) IODINE-BASED PARTICLES

(71) Applicant: Nanoprobes, Inc., Yaphank, NY (US)

(72) Inventor: James F. Hainfeld, Shoreham, NY (US)

(73) Assignee: NANOPROBES, INC., Yaphank, NY (US)

( * ) Notice: Subject to any disclaimer, the term of this patent is extended or adjusted under 35 U.S.C. 154(b) by 0 days.

(21) Appl. No.: 15/469,283

(22) Filed: Mar. 24, 2017

(65) Prior Publication Data

US 2017/0274101 A1 Sep. 28, 2017

Related U.S. Application Data

(60) Provisional application No. 62/313,364, filed on Mar. 25, 2016.

(51) Int. Cl.
*A61K 49/04* (2006.01)
*A61K 9/51* (2006.01)

(52) U.S. Cl.
CPC ........ *A61K 49/0438* (2013.01); *A61K 9/5146* (2013.01); *A61K 49/0442* (2013.01); *A61K 49/0485* (2013.01)

(58) Field of Classification Search
None
See application file for complete search history.

(56) References Cited

U.S. PATENT DOCUMENTS

| | | |
|---|---|---|
| 4,107,286 A | 8/1978 | Tilly et al. |
| 4,225,577 A | 9/1980 | Tilly et al. |
| 4,406,878 A | 9/1983 | Deboer |
| 4,474,747 A | 10/1984 | Dimo et al. |
| 4,877,600 A | 10/1989 | Bonnemain et al. |
| 5,043,152 A | 8/1991 | Schaefer et al. |
| 5,049,667 A | 9/1991 | Schaefer et al. |
| 5,250,672 A | 10/1993 | Sadler et al. |
| 5,374,416 A | 12/1994 | Rousseaux et al. |
| 5,417,960 A | 5/1995 | Schaefer et al. |
| 5,516,503 A | 5/1996 | Bourgouin et al. |
| 5,545,397 A | 8/1996 | Spielvogel et al. |
| 5,609,851 A | 3/1997 | Bennani et al. |
| 5,616,798 A | 4/1997 | Dugast-Zrihen et al. |
| 5,618,977 A | 4/1997 | Dugast-Zrihen et al. |
| 5,645,818 A | 7/1997 | Jackels et al. |
| 5,693,311 A | 12/1997 | Petta et al. |
| 5,709,846 A | 1/1998 | Lem et al. |
| 5,712,389 A | 1/1998 | Meyer et al. |
| 5,817,873 A | 10/1998 | Meyer et al. |
| 5,851,511 A | 12/1998 | Le et al. |
| 5,871,713 A | 2/1999 | Meyer et al. |
| 5,886,158 A | 3/1999 | Meyer et al. |
| 5,886,169 A | 3/1999 | Paris et al. |
| 5,919,432 A | 7/1999 | Meyer et al. |
| 7,049,476 B1 | 5/2006 | O'Lenick, Jr. |
| 8,734,830 B2 * | 5/2014 | Hwang ............... B01J 2/04 424/423 |
| 9,388,125 B2 | 7/2016 | Purohit et al. |
| 2004/0258744 A1 | 12/2004 | Counsell et al. |
| 2014/0099007 A1 | 4/2014 | Sarkar et al. |
| 2014/0328756 A1 | 11/2014 | Radeke et al. |
| 2015/0290344 A1 * | 10/2015 | Alexis ............ A61K 49/0442 424/9.451 |

FOREIGN PATENT DOCUMENTS

| | | | |
|---|---|---|---|
| CN | 105348410 A * | 2/2016 | |
| EP | 0188535 B1 | 8/1990 | |
| EP | 0809519 B1 * | 9/2002 | ......... A61K 49/0442 |
| WO | WO-95229951 A1 | 8/1995 | |
| WO | WO-9600088 A1 | 1/1996 | |
| WO | WO-2017165841 A1 | 9/2017 | |

OTHER PUBLICATIONS https://www.sigmaaldrich.com/catalog/product/aldrich/39391?lang=en®ion=US&gclid=EAIaIQobChMIrin4ydvZKw4gIVBkCGCh2v9AH8EAAYASAAEgJwFfD_BwE (Year: 2019).*
https://en.wikipedia.org/wiki/1-Ethyl-3-(3-dimethylaminopropyl)carbodiimide (Year: 2019).*
Bogdar et al. "Preparation and Characterization of Chitosan-Based Nanoparticles", Biomacromolecules 2005, 6, 2521-2527 (Year: 2005).*
Lim et al. "Iodinated Photosensitizing Chitosan: Self-Assembly into Tumor-Homing Nanoparticles with Enhanced Singlet Oxygen Generation", Bioconjugate Chem. 2012, 23, 1022-1028 (Year: 2012).*
Machine Translation of CN 105348410A, Printed From Web Apr. 27, 2020 (Year: 2020).*
PCT/US2017/024132 International Search Report and Written Opinion dated Jun. 30, 2017.

* cited by examiner

*Primary Examiner* — James W Rogers
(74) *Attorney, Agent, or Firm* — Wilson Sonsini Goodrich & Rosati

(57) ABSTRACT

Described herein are iodine-based particles which can be used as contrast agents for x-ray radiology. Also described herein are methods, software modules and hardware modules for imaging iodine-based particles.

4 Claims, 12 Drawing Sheets

(b)

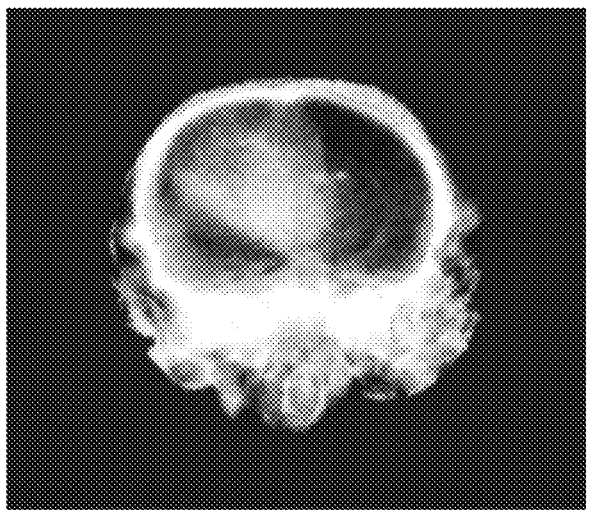 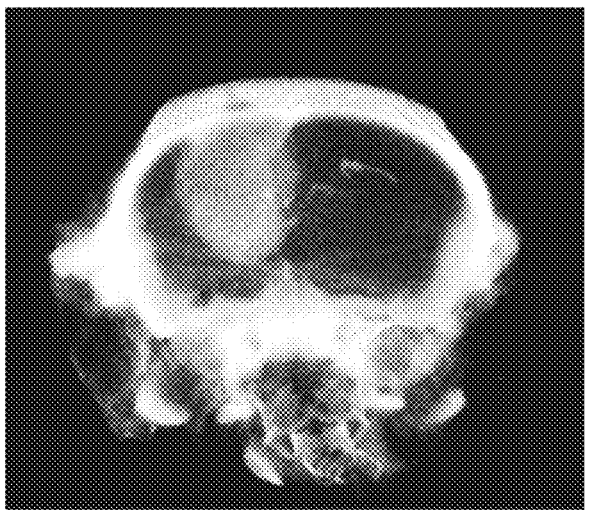
FIG. 10A                         FIG. 10B

IODINE-BASED PARTICLES

CROSS-REFERENCE

This application claims the benefit of U.S. Provisional Application No. 62/313,364, filed 25 Mar. 2016, which application is incorporated herein by reference.

BACKGROUND OF THE INVENTION

Presently, commercially available iodine-based x-ray contrast agents are cleared rapidly from the body through the kidneys. To be effective, high concentrations of these contrast agents are administered to patients to obtain adequate contrast. Unfortunately, all of these agents are nephrotoxic. Patients with poor kidney function can have their kidneys permanently damaged due to these commercially available iodine-based x-ray contrast agents. In fact, radiocontrast-induced nephropathy is a common cause of hospital acquired acute renal failure.

SUMMARY OF THE INVENTION

A need for contrast agents that do not present a danger to patients with poor kidney function has been recognized. An extended blood half-life contrast agent would be beneficial for improved medical imaging and diagnosis, particularly for abnormal vascular conditions such as cardiovascular disease and cancer detection. An extended blood half-life contrast agent that absorbs X-rays and is targeted to tumors would be beneficial in enhancing the effects of radiotherapy.

Described herein are iodine-based particles which can be used as contrast agents for x-ray radiology. Also described herein are methods, software modules and hardware modules for imaging iodine-based particles.

One aspect described herein is an iodine nanoparticle which is a reaction product of functionalized triiodobenzene, linking monomers, and biocompatible polymers; wherein said functionalized triiodobenzene, said linking monomers, and said biocompatible polymers are covalently cross-linked resulting in the structure of said nanoparticle being non-dendritic, non-uniform, and non-linear; wherein said nanoparticle has a polydispersity index of about 0.5 or less; wherein said nanoparticle has sufficient iodine density to be imaged by an imaging device following administration to a subject; and wherein said nanoparticle provides for an extended blood half-life.

In one embodiment, the functionalized triiodobenzene is functionalized 1,3,5-triiodobenzene or functionalized 2,4,6-triiodobenzene. In one embodiment, the functionalized triiodobenzene has the structure:

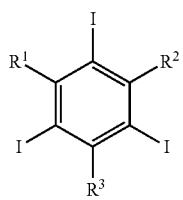

wherein $R^1$, $R^2$, and $R^3$ are each independently selected from a group consisting of optionally substituted alkyl, optionally substituted alkenyl, optionally substituted alkynyl, optionally substituted cycloalkyl, optionally substituted aryl, optionally substituted heteroaryl, optionally substituted alkoxy, optionally substituted aryloxy, optionally substituted amino, optionally substituted thiol, and optionally substituted phosphonate.

In one embodiment, the functionalized triiodobenzene is 2,4,6-triiodophenol, 2-(2,4,6-triiodophenoxy)ethanol, 2-(2-bromoethoxy)1,3,5-triiodobenzene, (2,4,6-triiodophenoxy)acetamide, 2-(2,4,6-triiodophenoxy)ethanesulfonic acid, 3-hydroxy-2,4,6-triiodobenzoic acid, 3-amino-2,4,6-triiodobenzoic acid, methyl 2-(2,4,6-triiodophenoxy)butyrate, (2-(2,4,6-triiodophenoxy)-ethyl)trimethylammonium methanesulfonate, 5-amino-2,4,6-triiodoisophthalic acid, α-ethyl-3-hydroxy-2,4,6-triiodohydrocinnamic acid, iopanoic acid, 7-(3-amino-2,4,6-triiodophenyl)heptanoic acid, 7-(3-amino-2,4,6-triiodophenyl)heptanoic acid ethyl ester, 2-phenyl-2-(2,4,6-triiodophenoxy)acetic acid, (2-(3-hydroxy-2,4,6-triiodobenzyl)butyrylamino)acetic acid, N-(2-dimethylaminoethyl)-2-(3-hydroxy-2,4,6-triiodobenzyl)butyramide, (2-(3-hydroxy-2,4,6-triiodobenzyl)butyrylamino)acetic acid ethyl ester, 3-(acetylamino)-5-[acetyl(methyl)amino]-2,4,6-triiodobenzoic acid, amidotrizoic acid, 3-acetamido-2,4,6-triiodobenzoic acid, bis(2-hydroxyethyl)-ammonium salt, 3-acetamido-2,4,6-triiodobenzoic acid, sodium salt dihydrate, 2-(3-hydroxy-2,4,6-triiodobenzyl)-N-(1-phenylethyl)butyramide, sodium diatrizoate hydrate, 3-(4-HO-Ph)-2-(2-(3-hydroxy-2,4,6-triiodobenzyl)-butyrylamino)propionic acid, 3-(acetylamino)-5-{[(2-hydroxyethyl)amino]carbonyl}-2,4,6-triiodobenzoic acid, 2-(3-hydroxy-2,4,6-triiodobenzyl)-N-(2-trifluoromethylphenyl)butyramide, meglumine diatrizoate, 3-acetamido-2,4,6-triiodobenzoic acid with 1-deoxy-1-(Me-amino)-glucit, 5-(N-2,3-dihydroxypropyl acetamido)-2,4,6-triiodo-N,N'-bis(2,3-dihydroxypropyl) isophthalamide, (2-(2-(3-hydroxy-2,4,6-triiodobenzyl)butyrylamino)thiazol-4-yl)acetic acid, 5-(N-2,3-dihydroxypropylacetamido)-2,4,6-triiodo-N,N'-bis(2,3-dihydroxypropyl) isophthalamide, 5-[N-(propylacetamido]-2,4,6-triiodo-N,N'-bis(propyl)isophthalamide, or any combination thereof.

In one embodiment, the linking monomers are diaminoethane, diaminopropane, triamine, ethereal tetraamine, diisopropyl ethylamine, polyethyleneimine, 1-ethyl-3-(3-dimethylaminopropyl)carbodiimide, dicarboxyethane, suberic acid, tricarboxylic acid, citrate, carboxycellulose, alginic acid, acrylic acid, carboxydextran, diethylenetriaminepentaacetic dianhydride, carbohydrazide, succinic dihydrazide, adipic acid dihydrazide, diglycidyl ether, 1,4-butadioldiglycidylether, polyethylene glycol diglycidyl, ethylene diamine, polyethylene amine, 1,1'-carbonyldiimidazole, or any combination thereof. In one embodiment, the linking monomers are carbohydrazide, succinic dihydrazide, diethylenetriaminepentaacetic dianhydride, adipic acid dihydrazide, diglycidyl ether, 1,4-butadioldiglycidylether, polyethylene glycol diglycidyl, ethylene diamine, polyethylene amine, 1,1'-carbonyldiimidazole, oxalyldihydrazide or any combination thereof.

In one embodiment, the biocompatible polymers are amine functionalized poly-N-vinylpyrrolidinone, polyvinyl alcohol, polysulfone, polyethylene terephthalate, polyetherurethanes, methoxy-polyethylene glycol, polyethyleneglycol-amine, polydimethylsiloxane, ethylene-co-vinylacetate, polymethylmethacrylate, polytetrafluoroethylene, polypropylene, polyethylene, alginic acid, polylysine, or any combination thereof. In one embodiment, the biocompatible polymers comprises polyglycolide, polylactide, polylactide-co-glycolide, polycaprolactone, polybutylene succinate and its copolymers, poly-p-dioxanone, polycarbonate, aromatic copolyesters, polyamides, polyester-amides, polyurethane, polyphosphazenes, polyphosphoesters, or any combination thereof.

In one embodiment, the biocompatible polymers are collagen, albumin, gluten, chitosan, hyaluronate, cellulose, alginate, gelatin, starch or any combination thereof.

In one embodiment, the iodine nanoparticle has a diameter from about 1 mm to about 100 mm, from about 1 mm to about 50 mm, from about 0.25 μm to about 100 μm, from about 0.25 μm to about 50 μm, from about 0.25 μm to about 30 μm, from about 1 nm to about 500 nm, from about 1 nm to about 250 nm, from about 1 nm to about 150 nm, from about 1 nm to about 100 nm, from about 1 nm to about 70 nm from about 1 nm to about 50 nm, from about 1 nm to about 40 nm, from about 1 nm to about 30 nm from about 5 nm to about 30 nm, or from about 10 nm to about 30 nm.

In one embodiment, the iodine nanoparticle has a diameter from about 1 mm to about 100 mm, from about 1 mm to about 50 mm, from about 0.25 μm to about 100 μm, from about 0.25 μm to about 50 μm, from about 0.25 μm to about 30 μm, from about 1 nm to about 500 nm, from about 1 nm to about 250 nm, from about 1 nm to about 150 nm, from about 1 nm to about 100 nm, from about 1 nm to about 70 nm, from about 1 nm to about 50 nm, from about 1 nm to about 40 nm, from about 1 nm to about 30 nm, from about 5 nm to about 30 nm, or from about 10 nm to about 30 nm. In one embodiment, In some embodiments of the iodine nanoparticle, the iodine nanoparticle has a diameter from about 1 nm or more, from about 10 nm or more, from about 20 nm or more, from about 30 nm or more, from about 40 nm or more, from about 50 nm or more, from about 60 nm or more, from about 70 nm or more, from about 80 nm or more, from about 90 nm or more, from about 300 nm or less, from about 275 nm or less, from about 250 nm or less, from about 200 nm or less, from about 175 nm or less, from about 150 nm or less, from about 125 nm or less, from about 100 nm or less, from about 90 nm or less, from about 80 nm or less, from about 70 nm or less, from about 60 nm or less, from about 50 nm or less, from about 40 nm or less, from about 30 nm or less, from about 20 nm or less, from about 10 nm or less, from about 1 nm to about 300 nm, from about 1 nm to about 250 nm, from about 1 nm to about 200 nm, from about 1 nm to about 150 nm, from about 1 nm to about 125 nm, from about 1 nm to about 100 nm, from about 1 nm to about 90 nm, from about 1 nm to about 80 nm, from about 1 nm to about 70 nm, from about 1 nm to about 60 nm, from about 1 nm to about 50 nm, from about 1 nm to about 40 nm, from about 1 nm to about 30 nm, from about 5 nm to about 30 nm, or from about 10 nm to about 30 nm. In some embodiments, the iodine nanoparticle has a diameter from about 1 mm to about 10 mm, from about 1 mm to about 5 mm, from about 0.25 μm to about 1000 μm, from about 0.25 μm to about 50 μm, from about 0.25 μm to about 30 μm, from about 1 nm to about 500 nm, from about 1 nm to about 250 nm, or from about 1 nm to about 50 nm.

One aspect described herein is an encapsulated iodine particle comprising a hydrophobic core and an amphipathic encapsulating layer wherein said hydrophobic core consists of a hydrophobic iodine nanoparticle, a hydrophobic triiodobenzene monomer or a hydrophobic triiodobenzene dimer; wherein said iodine nanoparticle is a reaction product of functionalized triiodobenzene and linking monomers; wherein said functionalized triiodobenzene and said linking monomers are covalently cross-linked resulting in the structure of said iodine nanoparticle being non-dendritic, non-uniform, and non-linear; wherein said iodine nanoparticle has a polydispersity index of about 0.5 or less; wherein said iodine nanoparticle has sufficient iodine density to be imaged by an imaging device following administration to a subject; and wherein said iodine nanoparticle provides for an extended blood half-life.

In one embodiment, the functionalized triiodobenzene is functionalized 1,3,5-triiodobenzene or functionalized 2,4,6-triiodobenzene. In one embodiment, the functionalized triiodobenzene has the structure:

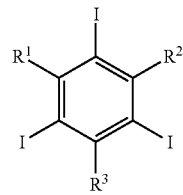

wherein $R^1$, $R^2$, and $R^3$ are each independently selected from a group consisting of optionally substituted alkyl, optionally substituted alkenyl, optionally substituted alkynyl, optionally substituted cycloalkyl, optionally substituted aryl, optionally substituted heteroaryl, optionally substituted alkoxy, optionally substituted aryloxy, optionally substituted amino, optionally substituted thiol, and optionally substituted phosphonate.

In one embodiment, the functionalized triiodobenzene is 2,4,6-triiodophenol, 2-(2,4,6-triiodophenoxy)ethanol, 2-(2-bromoethoxy)1,3,5-triiodobenzene, (2,4,6-triiodophenoxy) acetamide, 2-(2,4,6-triiodophenoxy)ethanesulfonic acid, 3-hydroxy-2,4,6-triiodobenzoic acid, 3-amino-2,4,6-triiodobenzoic acid, methyl 2-(2,4,6-triiodophenoxy)butyrate, (2-(2,4,6-triiodophenoxy)-ethyl)trimethylammonium methanesulfonate, 5-amino-2,4,6-triiodoisophthalic acid, α-ethyl-3-hydroxy-2,4,6-triiodohydrocinnamic acid, iopanoic acid, 7-(3-amino-2,4,6-triiodophenyl)heptanoic acid, 7-(3-amino-2,4,6-triiodophenyl)heptanoic acid ethyl ester, 2-phenyl-2-(2,4,6-triiodophenoxy)acetic acid, (2-(3-hydroxy-2,4,6-triiodobenzyl)butyrylamino)acetic acid, N-(2-dimethylaminoethyl)-2-(3-hydroxy-2,4,6-triiodobenzyl) butyramide, (2-(3-hydroxy-2,4,6-triiodobenzyl) butyrylamino)acetic acid ethyl ester, 3-(acetylamino)-5-[acetyl(methyl)amino]-2,4,6-triiodobenzoic acid, amidotrizoic acid, 3-acetamido-2,4,6-triiodobenzoic acid, bis(2-hydroxyethyl)-ammonium salt, 3-acetamido-2,4,6-triiodobenzoic acid, sodium salt dihydrate, 2-(3-hydroxy-2,4,6-triiodobenzyl)-N-(1-phenylethyl)butyramide, sodium diatrizoate hydrate, 3-(4-HO-Ph)-2-(2-(3-hydroxy-2,4,6-triiodobenzyl)-butyrylamino)propionic acid, 3-(acetylamino)-5-{[(2-hydroxyethyl)amino]carbonyl}-2,4,6-triiodobenzoic acid, 2-(3-hydroxy-2,4,6-triiodobenzyl)-N-(2-trifluoromethylphenyl)butyramide, meglumine diatrizoate, 3-acetamido-2,4,6-triiodobenzoic acid with 1-deoxy-1-(Me-amino)-glucit, 5-(N-2,3-dihydroxypropyl acetamido)-2,4,6-triiodo-N,N'-bis(2,3-dihydroxypropyl) isophthalamide, (2-(2-(3-hydroxy-2,4,6-triiodobenzyl)butyrylamino)thiazol-4-yl)acetic acid, 5-(N-2,3-dihydroxypropylacetamido)-2,4,6-triiodo-N,N'-bis(2,3-dihydroxypropyl) isophthalamide, 5-[N-(propylacetamido]-2,4,6-triiodo-N,N'-bis(propyl)isophthalamide, or any combination thereof.

In one embodiment, the linking monomers are diaminoethane, diaminopropane, triamine, ethereal tetraamine, diisopropyl ethylamine, polyethyleneimine, I-ethyl-3-(3-dimethylaminopropyl)carbodiimide, dicarboxyethane, suberic acid, tricarboxylic acid, citrate, carboxycellulose, alginic acid, acrylic acid, carboxydextran, diethylenetriaminepentaacetic dianhydride, carbohydrazide, succinic dihydrazide, adipic acid dihydrazide, diglycidyl ether, 1,4-butadioldiglycidylether, polyethylene glycol diglycidyl, ethylene diamine, polyethylene amine, 1,1'-carbonyldiimidazole, alkylamines, dodecylamine, oleylamine, octaoic hydrazide, or any combination thereof.

The encapsulated iodine particle according to claim 30 wherein said linking monomers are carbohydrazide, succinic dihydrazide, diethylenetriaminepentaacetic dianhydride, adipic acid dihydrazide, diglycidyl ether, 1,4-butadioldiglycidylether, polyethylene glycol diglycidyl, ethylene diamine, polyethylene amine, 1,1'-carbonyldiimidazole, oxalyldihydrazide, or any combination thereof. In one embodiment, the amphipathic polymer is polyethylene glycol, poly-D,L-lactic-coglycolic acid, polyethylene glycol-poly lactic acid, polyethylene glycol-polyepsilon-caprolactone, polysorbates, polyvinyl alcohol, polyvinyl pyrrolidone, dextran, chitosan, alginic acid, carboxycellulose, or any combination thereof.

In one embodiment, the encapsulated iodine particle has a diameter from about 1 mm to about 100 mm, from about 1 mm to about 50 mm, from about 0.25 µm to about 100 µm, from about 0.25 µm to about 50 m, from about 0.25 µm to about 30 µm, from about 1 nm to about 500 nm, from about 1 nm to about 250 nm, or from about 1 nm to about 50 nm.

One aspect described herein is the use of the iodine nanoparticle or the encapsulated iodine particle for radiotherapy enhancement. In one embodiment, the iodine nanoparticle or the encapsulated iodine particle is injected intravenously or locally into a body tissue and the tissue is subjected to irradiation. In one embodiment, the tissue is cancerous. In one embodiment, the irradiation is x-rays, visible light, lasers, infrared, microwave, radio frequencies, ultraviolet radiation, ultrasound, electrons, protons, ion beams, carbon ions, neutrons, or radioactive elements.

One aspect described herein is a method of producing enhanced imaging by exposing the iodine nanoparticle or the encapsulated iodine particle to radiation. In one embodiment, the radiation is x-rays, visible light, lasers, infrared, microwave, radio frequencies, ultraviolet radiation, ultrasound, electrons, protons, ion beams, carbon ions, neutrons, or radioactive elements.

One aspect described herein is a computer-implemented system comprising: a digital processing device comprising: at least one processor, an operating system configured to perform executable instructions, a memory, and a computer program including instructions executable by the digital processing device to create an application that provides improved iodine nanoparticle imaging, wherein the application comprises:
  a) a software module or hardware module collecting raw image data from an X-ray imaging device;
  b) a software module or hardware module removing or greatly reducing motion in said image data;
  c) a software module or hardware module increasing contrast in said image data; and
  d) a software module or hardware module automatically generating a processed image.

A computer-implemented system comprising: a digital processing device comprising: at least one processor, an operating system configured to perform executable instructions, a memory, and a computer program including instructions executable by the digital processing device to create an application that provides improved iodine nanoparticle imaging, wherein the application comprises:
  a) a software module or hardware module collecting raw image data from an X-ray imaging device;
  b) a software or hardware module averaging images over time to reduce noise;
  c) a software or hardware module increasing contrast in said image data; and
  d) a software or hardware module automatically generating a processed image.

A computer-implemented system comprising: a digital processing device comprising: at least one processor, an operating system configured to perform executable instructions, a memory, and a computer program including instructions executable by the digital processing device to create an application that provides improved iodine nanoparticle imaging, wherein the application comprises:
  a) a software module or hardware module collecting raw image data from an X-ray imaging device;
  b) a software module or hardware module removing or greatly reducing motion in said image data;
  c) a software module or hardware module averaging images over time to reduce noise;
  d) a software module or hardware module increasing contrast in said image data; and
  e) a software module or hardware module automatically generating a processed image.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6A is before an intravenous injection and FIG. 6B is 3 minutes after an intravenous injection, showing an increase in radiodensity. The mouse was injected with the polymer prepared in Example 1 with an effective dose of 1.6 g iodine/kg.

FIG. 7A shows a mouse injected with the polymer prepared in Example 1 size selected to be greater than 50 kDaltons, at an effective dose of 1.6 g iodine/kg. This image was obtained 42 minutes after injection. FIG. 7B shows a mouse injected with nanoparticles prepared in Example 1, but size selecting the fraction of low molecular weight polymer produced, between 10 kDaltons and 50 kDaltons, at an effective dose of 600 mg iodine/kg. This image was obtained 22 minutes after injection. The accumulation of iodine in the bladder is highlighted by an arrow.

FIG. 8A shows a mouse injected with the polymer prepared in Example 1 at an effective dose of 1.75 g iodine/kg. This image was obtained two minutes after injection. FIG. 8B shows a mouse injected with a standard iodine contrast agent (Iohexol) at an effective dose of 2.5 g iodine/kg. This image was obtained two minutes after injection.

FIG. 9A shows a mouse injected with the polymer prepared in Example 1 at an effective dose of 1.75 g iodine/kg. This image was obtained 30 minutes after injection. FIG. 9B shows a mouse injected with a standard iodine contrast agent (Iohexol) at an effective dose of 1.75 g iodine/kg. This image was obtained 30 minutes after injection.

FIGS. 10A and 10B show the microCT images of a mouse brain with a glioma brain tumor. FIG. 10A is an image obtained 1 day after intravenous injection of nanoparticles at a dose of 2.8 g iodine/kg. FIG. 10B is an image obtained 3 days after intravenous injection of nanoparticles at a dose of 2.8 g iodine/kg.

DETAILED DESCRIPTION OF THE INVENTION

Iodine Nanoparticle

Figure 1:
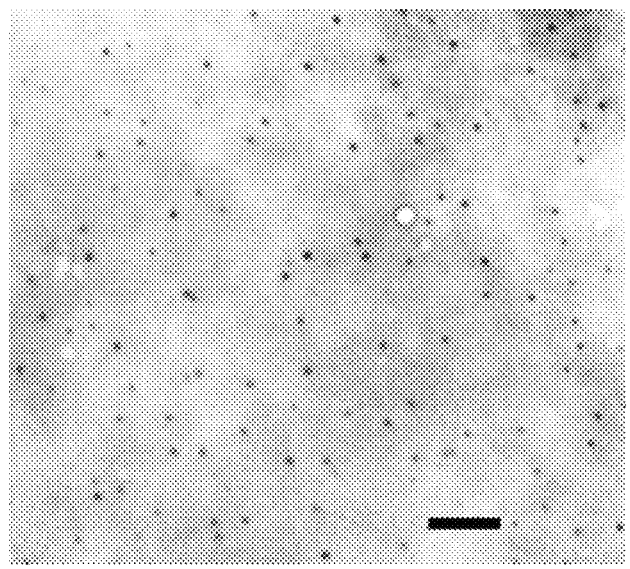
FIG. 1 is an electron micrograph of the polymer prepared in Example 1. Bar=500 nm.

As used herein, the term "iodine nanoparticle" refers to a reaction product of functionalized triiodobenzene, linking monomers, and biocompatible polymers; wherein said functionalized triiodobenzene, said linking monomers, and said biocompatible polymers are covalently cross-linked resulting in the structure of said iodine nanoparticle being non-dendritic, non-uniform, and non-linear; wherein said iodine nanoparticle has a polydispersity index of about 0.5 or less; wherein said iodine nanoparticle has sufficient iodine density to be imaged by an imaging device following administration to a subject; and wherein said iodine nanoparticle provides for an extended blood half-life.

As used herein, the term "functionalized triiodobenzene" refers to either functionalized 1,3,5-triiodobenzene or functionalized 2,4,6-triiodobenzene. In some embodiments, functionalized triiodobenzene has the structure:

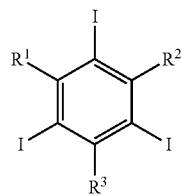

wherein $R_1$, $R_2$, and $R_3$ are each independently selected from a group consisting of optionally substituted alkyl, optionally substituted alkenyl, optionally substituted alkynyl, optionally substituted cycloalkyl, optionally substituted aryl, optionally substituted heteroaryl, optionally substituted alkoxy, optionally substituted aryloxy, optionally substituted amino, optionally substituted thiol, and optionally substituted phosphonate.

As used herein, the term "alkyl" refers to substituted or unsubstituted, straight and branched chain alkyl radicals containing from one to fifteen carbon atoms. The may be both straight and branched chain alkyl radicals containing from one to six carbon atoms and includes methyl, ethyl, propyl, isopropyl, butyl, isobutyl, tert-butyl and the like. The alkyl group may be optionally substituted with one or more substituents selected from halogen, —CN, —NO$_2$, —C(O)$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, phosphate, phosphonate, cycloalkyl, cycloalkenyl, aryl and heteroaryl.

As used herein, the term "optionally substituted alkenyl" refers to substituted or unsubstituted, straight and branched chain alkene radicals, including both the E- and Z-forms, containing from two to eight carbon atoms. The alkenyl group may be optionally substituted with one or more substituents selected from the group consisting of halogen, —CN, —NO$_2$, CO$_2$R, C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, S(O)R, SO$_2$R, —SO$_3$R, —S(O)$_2$N(R$^N$)$_2$, phosphate, phosphonate, cycloalkyl, cycloalkenyl, aryl and heteroaryl.

As used herein, the term "optionally substituted alkynyl" refers to substituted or unsubstituted, straight and branched carbon chain containing from two to eight carbon atoms and having at least one carbon-carbon triple bond. The term alkynyl includes, for example ethynyl, 1-propynyl, 2-propynyl, 1-butynyl, 3-methyl-1-butynyl and the like. The alkynyl group may be optionally substituted with one or more substituents selected from halo, —CN, NO$_2$, CO$_2$R, C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, phosphate, phosphonate, cycloalkyl, cycloalkenyl, aryl and heteroaryl.

As used herein, the term "optionally substituted cycloalkyl" refers to substituted or unsubstituted cyclic alkyl radicals containing from three to twelve carbon atoms and includes cyclopropyl, cyclopentyl, cyclohexyl and the like. The term "cycloalkyl" also includes polycyclic systems having two rings in which two or more atoms are common to two adjoining rings (the rings are "fused"). The cycloalkyl group may be optionally substituted with one or more substituents selected from halogen, alkyl, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, —SiR$_3$, —P(O)R, phosphate, phosphonate, cycloalkyl, cycloalkenyl, aryl and heteroaryl.

As used herein, the term "optionally substituted aryl" refers to substituted or unsubstituted single-ring and multiple aromatic groups (for example, phenyl, pyridyl and pyrazole, etc.) and polycyclic ring systems (naphthyl and quinolinyl, etc.). The polycyclic rings may have two or more rings in which two atoms are common to two adjoining rings (the rings are "fused") wherein at least one of the rings is aromatic, e.g., the other rings can be cycloalkyls, cycloalkenyls, aryl, heterocycles and/or heteroaryls. The aryl group may be optionally substituted with one or more substituents selected from halogen, alkyl, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO₂R, —SO₃R, —S(O)₂N(R$^N$)₂, —SiR₃, —P(O)R, phosphate, phosphonate, cycloalkyl, cycloalkenyl, aryl and heteroaryl.

As used herein, the term "optionally substituted heteroaryl" refers to substituted or unsubstituted aromatic and non-aromatic cyclic radicals having at least one heteroatom as a ring member. Preferred heterocyclic groups are those containing five or six ring atoms which includes at least one hetero atom and includes cyclic amines such as morpholino, piperidino, pyrrolidine and the like and cyclic ethers, such as tetrahydrofuran, tetrahydropyran and the like. Aromatic heterocyclic groups, also termed "heteroaryl" groups, contemplates single-ring hetero-aromatic groups that may include from one to three heteroatoms, for example, pyrrole, furan, thiophene, imidazole, oxazole, thiazole, triazole, pyrazole, oxodiazole, thiadiazole, pyridine, pyrazine, pyridazine, pyrimidine and the like. The term heteroaryl also includes polycyclic hetero-aromatic systems having two or more rings in which two or more atoms are common to two adjoining rings (the rings are "fused") wherein at least one of the rings is a heteroaryl, e.g., the other rings can be cycloalkyls, cycloalkenyls, aryl, heterocycles and/or heteroaryls. Examples of polycyclic heteroaromatic systems include quinoline, isoquinoline, cinnoline, tetrahydroisoquinoline, quinoxaline, quinazoline, benzimidazole, benzofuran, benzothiophene, benzoxazole, benzothiazole, indazole, purine, benzotriazole, pyrrolepyridine, pyrrazolopyridine and the like. The heterocyclic group may be optionally substituted with one or more substituents selected from the group consisting halogen, alkyl, —CN, —NO₂, —CO₂R, —C(O)R, —O—R, —N(R$^N$)₂, —N(R$^N$)C(O)R, —N(R$^N$)S(O)₂R, —SR, —C(O)N(R$^N$)₂, —OC(O)R, —OC(O)N(R$^N$)₂, —SOR, —SO₂R, —SO₃R, —S(O)₂N(R$^N$)₂, —SiR₃, —P(O)R, phosphate, phosphonate, cycloalkyl, cycloalkenyl, aryl and heteroaryl.

As used herein, the term "optionally substituted alkoxy" refers to substituted or unsubstituted oxygen with a alkyl group as a substituent and includes methoxy, ethoxy, butoxy, trifluoromethoxy and the like. It also includes divalent substituents linked to two separated oxygen atoms such as, without limitation, —O—(CH₂)$_{1-4}$—O—, —O—CF₂—O—, —O—(CH₂)$_{1-4}$—O—(CH₂CH₂—O)$_{1-4}$— and —(O—CH₂CH₂—O)$_{1-4}$—.

As used herein, the term "optionally substituted aryloxy" refers to substituted or unsubstituted oxy with an aryl group as a substituent and includes phenyloxy, benzyloxy and the like.

As used herein, the term "optionally substituted amino" refers to a group of the structure —NR$^N$₂.

As used herein, the term "substituted thiol" refers to a thiol group having the hydrogen replaced with, for example a C$_{1-6}$ alkyl group ("—S(C$_{1-6}$ alkyl)"), an aryl ("—S(aryl)"), or an aralkyl ("—S(alkyl)(aryl)") and so on As used herein, the term "optionally substituted phosphonate" refers to the moieties having the following structures, respectively:

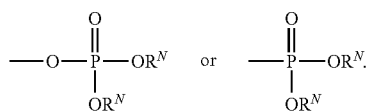

Each R$^N$ is independently selected from the group consisting of hydrogen, —OH, C₁ to C₁₂ alkyl, C₁ to C₁₂ heteroalkyl, alkenyl, alkynyl, cycloalkyl, heterocycle, aryl, heteroaryl, arylalkyl, alkoxy, alkoxycarbonyl, alkanoyl, carbamoyl, substituted sulfonyl, sulfonate and sulfonamide. Two R$^N$ may be taken together with C, O, N or S to which they are attached to form a five- to seven-membered ring which may optionally contain a further heteroatom.

In some embodiments the functionalized triiodobenzene is 2,4,6-triiodophenol, 2-(2,4,6-triiodophenoxy)ethanol, 2-(2-bromoethoxy)1,3,5-triiodobenzene, (2,4,6-triiodophenoxy)acetamide, 2-(2,4,6-triiodophenoxy)ethanesulfonic acid, 3-hydroxy-2,4,6-triiodobenzoic acid, 3-amino-2,4,6-triiodobenzoic acid, methyl 2-(2,4,6-triiodophenoxy)butyrate, (2-(2,4,6-triiodophenoxy)-ethyl)trimethylammonium methanesulfonate, 5-amino-2,4,6-triiodoisophthalic acid, α-ethyl-3-hydroxy-2,4,6-triiodohydrocinnamic acid, iopanoic acid, 7-(3-amino-2,4,6-triiodophenyl)heptanoic acid, 7-(3-amino-2,4,6-triiodophenyl)heptanoic acid ethyl ester, 2-phenyl-2-(2,4,6-triiodophenoxy)acetic acid, (2-(3-hydroxy-2,4,6-triiodobenzyl)butyrylamino)acetic acid, N-(2-dimethylaminoethyl)-2-(3-hydroxy-2,4,6-triiodobenzyl)butyramide, (2-(3-hydroxy-2,4,6-triiodobenzyl)butyrylamino)acetic acid ethyl ester, 3-(acetylamino)-5-[acetyl(methyl)amino]-2,4,6-triiodobenzoic acid, amidotrizoic acid, 3-acetamido-2,4,6-triiodobenzoic acid, bis(2-hydroxyethyl)-ammonium salt, 3-acetamido-2,4,6-triiodobenzoic acid, sodium salt dihydrate, 2-(3-hydroxy-2,4,6-triiodobenzyl)-N-(1-phenylethyl)butyramide, sodium diatrizoate hydrate. 3-(4-HO-Ph)-2-(2-(3-hydroxy-2,4,6-triiodobenzyl)-butyrylamino)propionic acid, 3-(acetylamino)-5-{[(2-hydroxyethyl)amino]carbonyl}-2,4,6-triiodobenzoic acid, 2-(3-hydroxy-2,4,6-triiodobenzyl)-N-(2-trifluoromethylphenyl)butyramide, meglumine diatrizoate, 3-acetamido-2,4,6-triiodobenzoic acid with 1-deoxy-1-(Me-amino)-glucit, 5-(N-2,3-dihydroxypropyl acetamido)-2,4,6-triiodo-N,N'-bis(2,3-dihydroxypropyl)isophthalamide, (2-(2-(3-hydroxy-2,4,6-triiodobenzyl)butyrylamino)thiazol-4-yl) acetic acid, 5-(N-2,3-dihydroxypropylacetamido)-2,4,6-triiodo-N,N'-bis(2,3-dihydroxypropyl)isophthalamide, 5-[N-(propylacetamido]-2,4,6-triiodo-N,N'-bis(propyl) isophthalamide, or any combination thereof.

As used herein, the term "linking monomers" refers to monomers that crosslink the functionalized triiodobenzene and/or the biocompatible polymers. In some embodiments, linking monomers are diaminoethane, diaminopropane, triamine, ethereal tetraamine, diisopropyl ethylamine, polyethyleneimine, 1-ethyl-3-(3-dimethylaminopropyl)carbodiimide, dicarboxyethane, suberic acid, tricarboxylic acid, citrate, carboxycellulose, alginic acid, acrylic acid, carboxydextran, diethylenetriaminepentaacetic dianhydride, carbohydrazide, succinic dihydrazide, adipic acid dihydrazide, diglycidyl ether, 1,4-butadioldiglycidylether, polyethylene glycol diglycidyl, ethylene diamine, polyethylene amine, 1,1'-carbonyldiimidazole, or any combination thereof. In some embodiments, linking monomers are carbohydrazide, succinic dihydrazide, diethylenetriaminepentaacetic dianhydride, adipic acid dihydrazide, diglycidyl ether, 1,4-butadioldiglycidylether, polyethylene glycol diglycidyl, ethylene diamine. polyethylene amine, 1,1'-carbonyldiimidazole, oxalyldihydrazide, or any combination thereof.

As used herein, the term "biocompatible polymer" refers to polymers that are synthetic or natural polymers which are tolerated by the body. In some embodiments, biocompatible polymers are amine functionalized poly-N-vinylpyrrolidinone, polyvinyl alcohol, polysulfone, polyethylene terephthalate, polyether-urethanes, methoxy-polyethylene glycol, polyethyleneglycol-amine, polydimethylsiloxane, ethyleneco-vinylacetate, polymethylmethacrylate, polytetrafluoroethylene, polypropylene, polyethylene, alginic acid, polylysine, polyglycolide, polylactide, polylactide-co-glycolide, polycaprolactone, polybutylene succinate and its copolymers, poly-p-dioxanone, polycarbonate, aromatic copolyesters, polyamides, polyester-amides, polyurethane, polyphosphazenes, polyphosphoesters, collagen, albumin, gluten, chitosan, hyaluronate, cellulose, alginate, gelatin, starch, or any combination thereof.

As used herein, the term "diameter" is used to describe the size of the polymer as determined from dynamic light scattering. In some embodiments, the iodine nanoparticle has a diameter from about 1 nm to about 1000 nm, about 1 nm to about 250 nm, or from about 1 nm to about 50 nm. In some embodiments, the iodine nanoparticle can be further polymerized to sizes of about 1 mm to about 10 mm, from about 1 mm to about 5 mm, from about 1 μm to about 1000 μm, from about 1 m to about 50 μm, or from about 1 μm to about 30 μm.

In some embodiments, to prepare the iodine nanoparticle, functionalized triiodobenzene is dissolved in water. In some embodiments, triiodobenzene is functionalized 1,3,5-triiodobenzene or functionalized 2,4,6-triiodobenzene. In some embodiments, functionalized triiodobenzene has the structure:

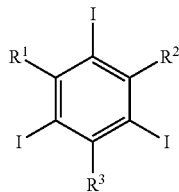

wherein $R_1$, $R_2$, and $R_3$ are each independently selected from a group consisting of optionally substituted alkyl, optionally substituted alkenyl, optionally substituted alkynyl, optionally substituted cycloalkyl, optionally substituted aryl, optionally substituted heteroaryl, optionally substituted alkoxy, optionally substituted aryloxy, optionally substituted amino, optionally substituted thiol, and optionally substituted phosphonate. In some embodiments, functionalized triiodobenzene is 2,4,6-triiodophenol, 2-(2,4,6-triiodophenoxy)ethanol, 2-(2-bromoethoxy)1,3,5-triiodobenzene, (2,4,6-triiodophenoxy)acetamide, 2-(2,4,6-triiodophenoxy)ethanesulfonic acid, 3-hydroxy-2,4,6-triiodobenzoic acid, 3-amino-2,4,6-triiodobenzoic acid, methyl 2-(2,4,6-triiodophenoxy)butyrate, (2-(2,4,6-triiodophenoxy)-ethyl)trimethylammonium methanesulfonate, 5-amino-2,4,6-triiodoisophthalic acid, α-ethyl-3-hydroxy-2,4,6-triiodohydrocinnamic acid, iopanoic acid, 7-(3-amino-2,4,6-triiodophenyl)heptanoic acid, 7-(3-amino-2,4,6-triiodophenyl)heptanoic acid ethyl ester, 2-phenyl-2-(2,4,6-triiodophenoxy)acetic acid, (2-(3-hydroxy-2,4,6-triiodobenzyl)butyrylamino)acetic acid, N-(2-dimethylaminoethyl)-2-(3-hydroxy-2,4,6-triiodobenzyl)butyramide, (2-(3-hydroxy-2,4,6-triiodobenzyl)butyrylamino)acetic acid ethyl ester, 3-(acetylamino)-5-[acetyl(methyl)amino]-2,4,6-triiodobenzoic acid, amidotrizoic acid, 3-acetamido-2,4,6-triiodobenzoic acid, bis(2-hydroxyethyl)-ammonium salt, 3-acetamido-2,4,6-triiodobenzoic acid, sodium salt dihydrate, 2-(3-hydroxy-2,4,6-triiodobenzyl)-N-(1-phenylethyl)butyramide, sodium diatrizoate hydrate, 3-(4-HO-Ph)-2-(2-(3-hydroxy-2,4,6-triiodobenzyl)-butyrylamino)propionic acid, 3-(acetylamino)-5-{[(2-hydroxyethyl)amino]carbonyl}-2,4,6-triiodobenzoic acid, 2-(3-hydroxy-2,4,6-triiodobenzyl)-N-(2-trifluoromethylphenyl)butyramide, meglumine diatrizoate, 3-acetamido-2,4,6-triiodobenzoic acid with 1-deoxy-1-(Me-amino)-glucit, 5-(N-2,3-dihydroxypropyl acetamido)-2,4,6-triiodo-N,N'-bis(2,3-dihydroxypropyl) isophthalamide, (2-(2-(3-hydroxy-2,4,6-triiodobenzyl)butyrylamino)thiazol-4-yl)acetic acid, 5-(N-2,3-dihydroxypropylacetamido)-2,4,6-triiodo-N,N'-bis(2,3-dihydroxypropyl) isophthalamide, 5-[N-(propylacetamido]-2,4,6-triiodo-N,N-bis(propyl)isophthalamide, or any combination thereof.

In some embodiments sodium metaperiodate is added to the solution of functionalized triiodobenzene in water. This mixture is reacted from about 10 minutes to about 24 hours. In some embodiments, the mixture is reacted from about 20 minutes to about 40 minutes. Then the excess sodium metaperiodate is optionally quenched with ethylene glycol. After quenching, the product mixture is dried under vacuum and then resuspended in water. To this solution, a linking monomer is added. In some embodiments, the linking monomers are diaminoethane, diaminopropane, triamine, ethereal tetraamine, diisopropyl ethylamine, polyethyleneimine, 1-ethyl-3-(3-dimethylaminopropyl)carbodiimide, dicarboxyethane, suberic acid, tricarboxylic acid, citrate, carboxycellulose, alginic acid, acrylic acid, carboxydextran, diethylenetriaminepentaacetic dianhydride, carbohydrazide, succinic dihydrazide, adipic acid dihydrazide, diglycidyl ether, 1,4-butadioldiglycidylether, polyethylene glycol diglycidyl, ethylene diamine, polyethylene amine, 1,1'-carbonyldiimidazole, or any combination thereof. In some embodiments, linking monomers are carbohydrazide, succinic dihydrazide, diethylenetriaminepentaacetic dianhydride, adipic acid dihydrazide, diglycidyl ether, 1,4-butadioldiglycidylether, polyethylene glycol diglycidyl, ethylene diamine, polyethylene amine, 1,1'-carbonyldiimidazole, oxalyldihydrazide, or any combination thereof.

Biocompatible polymers are then added to the reaction mixture. In some embodiments, biocompatible polymers are amine functionalized poly-N-vinylpyrrolidinone, polyvinyl alcohol, polysulfone, polyethylene terephthalate, polyetherurethanes, methoxy-polyethylene glycol, polyethyleneglycol-amine, polydimethylsiloxane, ethylene-co-vinylacetate, polymethylmethacrylate, polytetrafluoroethylene, polypropylene, polyethylene, alginic acid, polylysine, polyglycolide, polylactide, polylactide-co-glycolide, polycaprolactone, polybutylene succinate and its copolymers, poly-p-dioxanone, polycarbonate, aromatic copolyesters, polyamides, polyester-amides, polyurethane, polyphosphazenes, polyphosphoesters, collagen, albumin, gluten, chitosan, hyaluronate, cellulose, alginate, gelatin, starch, or any combination thereof. The reaction mixture is allowed to react for about 6 hours to about 24 hours. In one embodiment, the reaction mixture is allowed to react for about 12 hours to about 18 hours. Sodium borohyride is then added and the reaction mixture is allowed to react further for about 1 hour to about 5 hours. In one embodiment, the reaction mixture is allowed to react further for 2 hours to about 24 hours. The reaction mixture is then filtered and the iodine nanoparticle is obtained. The iodine nanoparticle is characterized using dynamic light scattering and electron microscopy.

Scheme 1 is one embodiment of the preparation of the iodine nanoparticle.

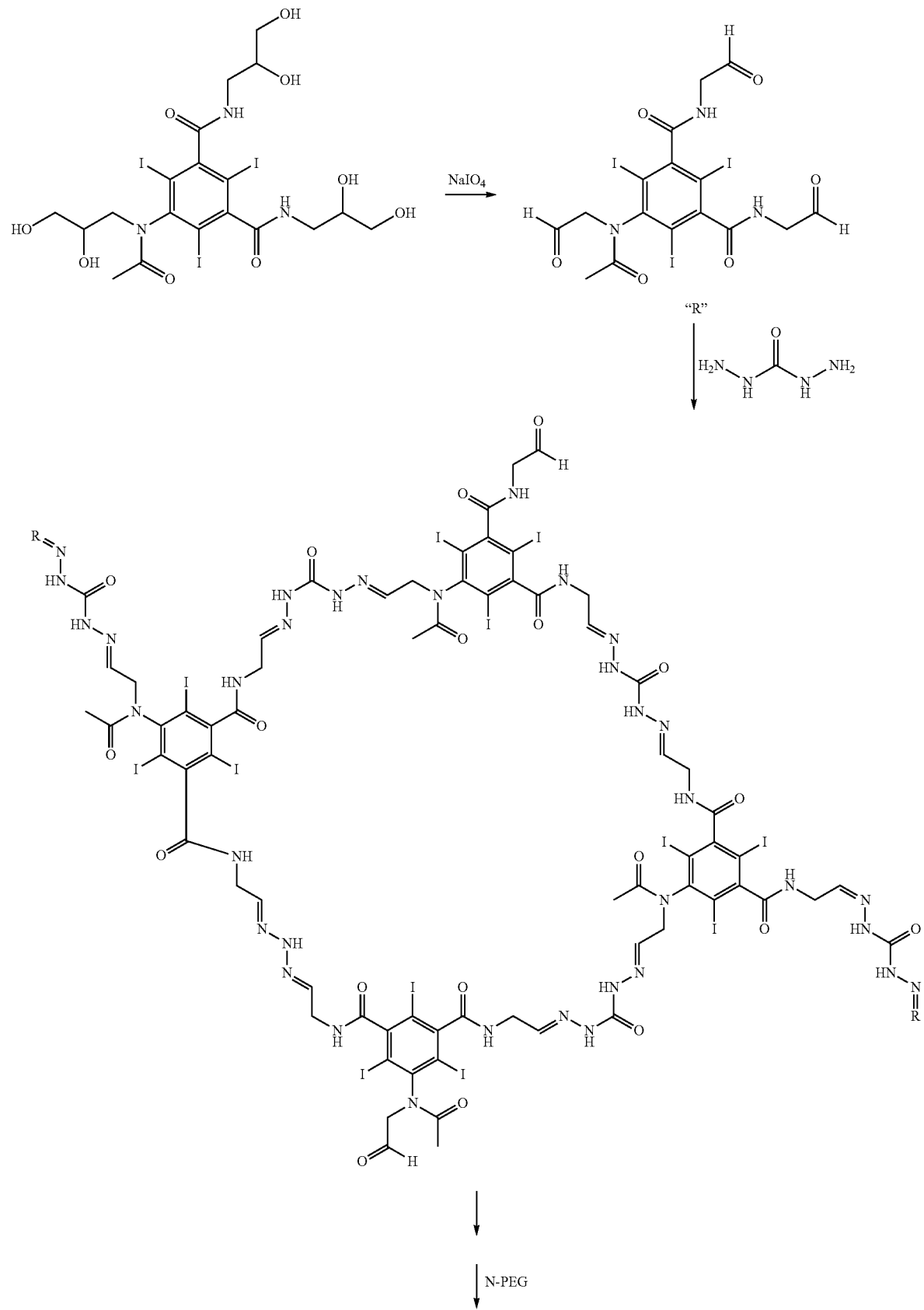

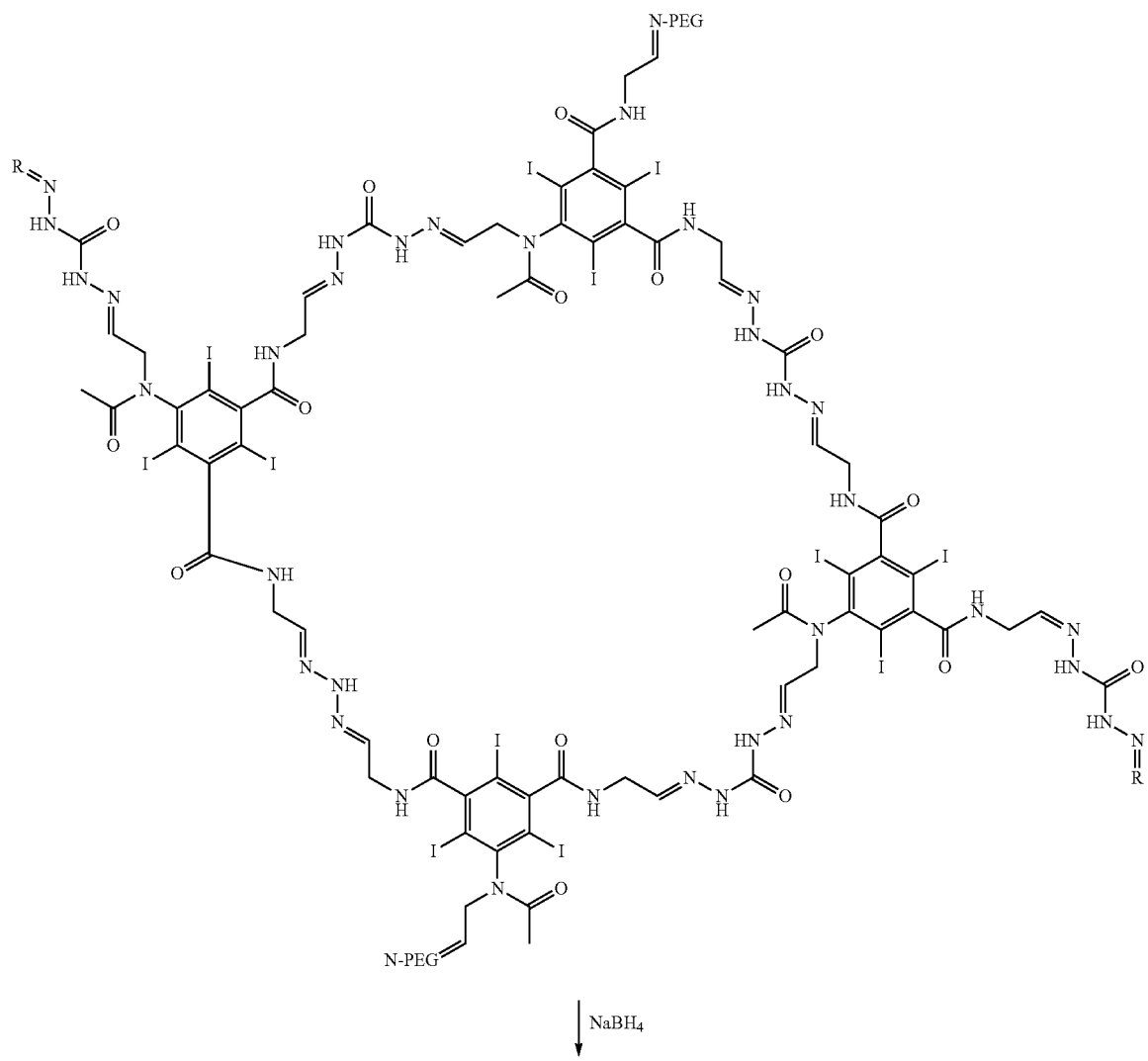

-continued

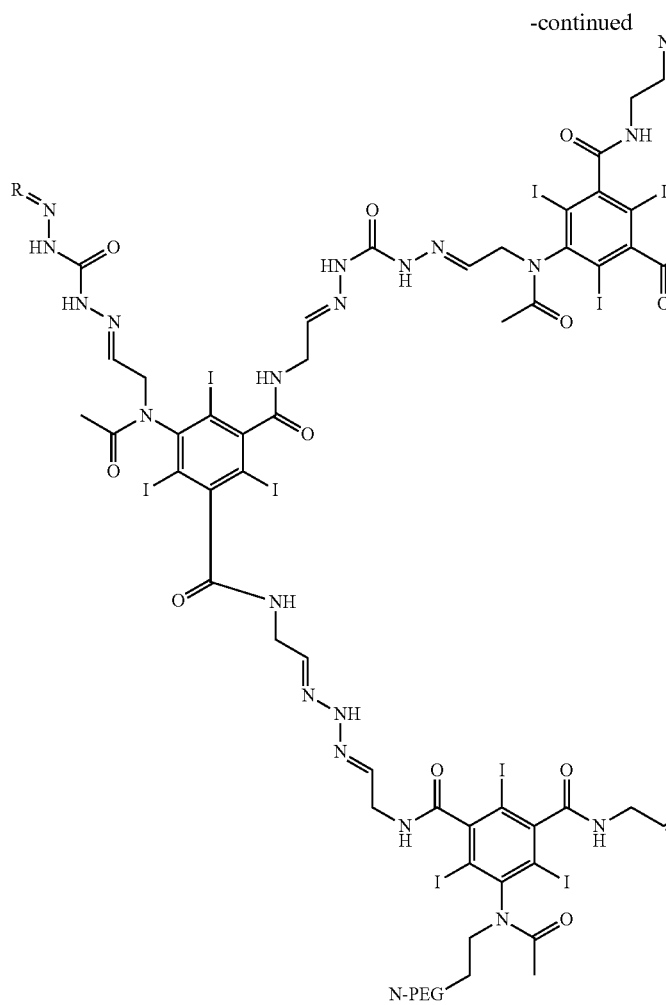
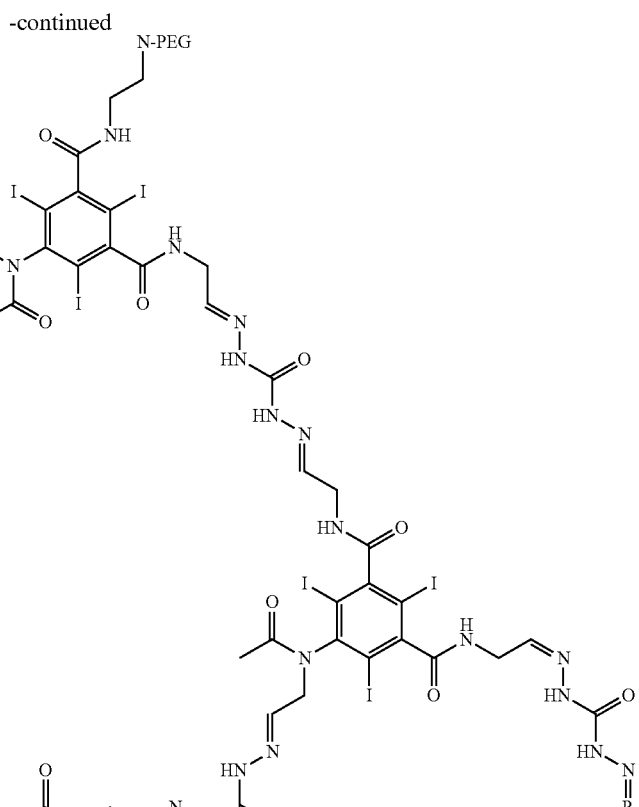

In one embodiment, the iodine nanoparticle is formulated as a liposome or encapsulated in one or more layers of surfactants. To prepare the liposomes, a biocompatible polymer is diluted with water. Then a solution of functionalized triiodobenzene is added and incubated with a base. In some embodiments the incubation is for about 0.5 hours to about 2 hours. Parallel to this, a hydrophobic solution is prepared. Then the mixture containing the biocompatible polymer and functionalized triiodobenzene is added to solution the hydrophobic solution. In one embodiment, addition occurs using a rotating blade homogenizer. The liposomes formed are then purified and collected for administration to a subject.

In one embodiment, the iodine nanoparticle is a dimer of functionalized triiodobenzene. To prepare the dimers, functionalized triiodobenzene is dissolved in a polar solvent. In one embodiment, the polar solvent is dimethylformamide. The solution of functionalized triiodobenzene is then reacted with a linking monomer. In one embodiment the linking monomer is 1-ethyl-3-(3-dimethylaminopropyl)carbodiimide. The product mixture is vacuum dried and then resuspended in hexane. An aqueous solution of a biocompatible polymer is added to the suspended product mixture and then heated. In one embodiment the mixture is heated at about 70° C. to about 90° C. In one embodiment the mixture is heated for about 0.5 hours to about 2 hours.

Encapsulated Iodine Particles

As used herein, the term "encapsulated iodine particles" comprises a core of hydrophobic iodine nanoparticle described herein, a hydrophobic triiodobenzene monomer or a hydrophobic dimer encapsulated by an amphipathic polymer. Said iodine nanoparticle is a reaction product of functionalized triiodobenzene, linking monomers and biocompatible polymers; wherein said functionalized triiodobenzene, said linking monomers, and said biocompatible polymers are covalently cross-linked resulting in the structure of said iodine nanoparticle being non-dendritic, non-uniform, and non-linear; wherein said iodine nanoparticle has a polydispersity index of about 0.5 or less; wherein said iodine nanoparticle has sufficient iodine density to be imaged by an imaging device following administration to a subject; and wherein said iodine nanoparticle provides for an extended blood half-life.

As used herein, the term "amphipathic polymer" refers to a polymer with hydrophobic and hydrophilic characteristics. In some embodiments, the amphipathic polymer is polyethylene glycol-poly-D,L-lactic-coglycolic acid, polyethylene glycol-poly lactic acid, polyethylene glycol-polyepsiloncaprolactone, polysorbates, polyvinyl alcohol, polyvinyl pyrrolidone, dextran, chitosan, alginic acid, carboxycellulose, or any combination thereof.

In some embodiments, the encapsulated iodine particle has a diameter from about 1 mm to about 100 mm, from about 1 mm to about 50 mm, from about 0.50 m to about 100

μm, from about 0.25 μm to about 50 μm, from about 0.25 μm to about 30 μm, from about 1 nm to about 500 nm, from about 1 nm to about 250 nm, or from about 1 nm to about 50 nm.

In some embodiments, to prepare the encapsulated iodine particles, the iodine nanoparticle is dissolved in a solvent. In some embodiments, the solvent is a non-aqueous polar solvent. In some embodiments, the non-aqueous polar solvent is dimethylsulfoxide, dimethylformamide, tetrahydrofuran, acetone, or acetonitrile. In some embodiments, the solvent is an organic solvent. In some embodiments, the organic solvent is dichloromethane, chloroform, cyclohexane, diethyl ether, hexane, xylene, ethyl acetate, or benzene. The amphipathic polymer is then added. In some embodiments the amphipathic polymer is polyethylene glycol-poly-D,L-lactic-coglycolic acid, polyethylene glycol-poly lactic acid, polyethylene glycol-polyepsilon-caprolactone, polysorbates, polyvinyl alcohol, polyvinyl pyrrolidone, dextran, chitosan, alginic acid, or carboxycellulose. This mixture is then added to a larger volume of liquid which contains water and optionally a water-soluble polymer. In some embodiments, the water-soluble polymer is polyvinyl alcohol or polyvinyl pyrrolidone. This final mixture is agitated to form an emulsion. In one embodiment, the agitation is by way of sonication. After agitation, the solvent is removed. In some embodiments, the solvent is removed by way of solvent extraction, vacuum drying, heat drying or freeze drying. The removal of solvent results in the encapsulated iodine particles which are characterized using dynamic light scattering and electron microscopy.

In some embodiments, the storage of the encapsulated iodine particles is at room temperature, at about 4° C., at about −20° C. or rapidly frozen in liquid nitrogen and then stored. In some embodiments, the storage of the encapsulated iodine particles occurs after the dried encapsulated iodine particles are resuspended in a biocompatible excipient. In one embodiment, the biocompatible excipient is phosphate buffered saline at about pH 7.4.

Methods and Uses

X-ray imaging has the advantage of having the highest spatial resolution. This resolution may be 1-10 μm in a microCT image, compared to about 2 mm in microPET and about 200 μm in microMRI. Clinical resolutions also show X-ray/CT imaging to be best. X-ray radiography and CT not only have important clinical applications in anatomical/physiological imaging, including angiography and tumor imaging, but also have advantages over PET and MRI in their relatively low cost, higher resolution, and greater availability.

The term "radiotherapy enhancement" refers to treatment using radiation that is improved or increased in some manner.

The term "radiation" refers to forms of radiation suitable for use and may include, but are not limited to, x-rays, radioactivity, electrons, protons, neutrons, ions, visible light, lasers, infrared, microwave, radio frequencies, ultraviolet radiation, other electromagnetic radiation at various frequencies, and ultrasound. X-rays can be produced electrons bombarding a target, by othovoltage equipment (less than 500 kVp), by synchrotrons, by linear accelerators, and with equipment producing X-rays in the 500 kV-100 MV range, or electrons in the 1-300 MeV range. Various other sources may be employed, including, but not limited to electrons, protons, ion beams, carbon ions, and neutrons. Many of these sources produce secondary effects that can be useful for the intended purpose of ablating a target tissue, for example, specific heating caused by energy absorption of the sample. Radioisotopes may also be used that have emissions favorable for iodine absorption, such as I-125, Yb-169, Au-198, Pd-103, Cs-137, Co-60, Ir-192.

Radiotherapy using the iodine nanoparticle or the encapsulated iodine particle can be further enhanced by spatially fractionated beams. A collimator, scan pattern, or other method can be used to produce an irradiation pattern that consists of peaks and valleys of dose. The peak and valley regions can be micrometers to centimeters in size. This spares the tissue first impinged upon since radiation leaves un-irradiated or less irradiated tissue allowing the tissue to heal. The source can be arranged or the energy used to spread out the beams with depth, eventually forming overlapping peak regions thus producing a more damaging and more continuous irradiation region. This region can be designed to cover various tumors at depth while better sparing normal tissue closer to the source. It also allows lower energy beams to be used to treat regions at deeper depths. Another variation is to irradiate spatially fractionated beams from two or various angles (cross-firing) such that they interleave in the target volume, creating a continuous or quasi-continuous beam there. This spares tissues outside the target volume which are exposed to spatially fractionated beams, but achieves a more damaging irradiation in the target volume where the beams are overlapped or interleaved creating essentially a more destructive continuous beam. Stereotactic irradiation of pencil-like beams may also be used to better focus the radiation on the treatment or tumor volume such as with the cyberknife or gamma-knife systems.

Radiotherapy using the iodine nanoparticle or the encapsulated iodine particle can be improved by applying the radiation from various directions (tomotherapy), but all focused on the target volume, compared to a unidirectional irradiation. This has the effect of spreading out the incident beam and sparing skin or other superficial tissues. Collimators are adjustable at the various irradiation directions to sculpt the dose topography. Mathematical treatment planning can be used to optimize the dose to the target region and minimize dose to surrounding and critical tissues or structures.

Current radiotherapy tries to focus the maximal dose on the central tumor site, using, for example, IMRT (Intensity Modulated RadioTherapy). However, although this strategy avoids ancillary damage, it leaves poorly irradiated surrounding areas that may contain migrated or metastasized tumor cells that will lead to recurrence. Recurrent cancers are more difficult to treat. In the method disclosed here, the iodine nanoparticle or encapsulated iodine particle are targeted to the tumor cells that have spread beyond the main tumor mass and will boost the radiation just near these tumor cells, since the tumor cells secrete vascular endothelial growth factor, vascular permeability factor, and other cytokines that stimulate angiogenesis and leaky blood vessels. Tumor targeting may also be by addition of other agents facilitating tumor uptake, such as RGD peptides, drugs, or ultrasound, or by attachment of targeting agents such as antibodies, peptides, or other targeting moieties to the iodine nanoparticle or encapsulated iodine particle. The volume of irradiation is expanded significantly from what would typically be irradiated, but at lower dose than that currently used. The dose will now be boosted only in tumor locations, enough to eradicate migrating tumor cells and greatly reducing the frequently deadly tumor recurrence. The irradiated volume can be increased 25% or more than that currently practiced with radiotherapy.

The methods described herein can be optionally combined with chemotherapy, immunotherapy, hyperthermia, ultrasound, high intensity focused ultrasound, X-ray therapy, proton therapy, carbon ion therapy, surgery, microwave therapy, and other therapies to result in a better treatment. In many cases, combination treatments show a synergistic effect where the combined treatment produces a better result than the sum of each therapy applied separately. For example, hyperthermia given at or near the same time as radiotherapy can greatly enhance the radiotherapy. Immunotherapy has been shown to be enhanced when combined with radiotherapy. Similarly, radiotherapy using the iodine nanoparticle or encapsulated iodine particle can enhance the effects of hyperthermia or immunotherapy. Radiotherapy using the iodine nanoparticle or encapsulated iodine particle can alter the microenvironment in a tumor resulting in better penetration and effectiveness of drugs. Radiotherapy using the iodine nanoparticle or encapsulated iodine particle allows immune cells better access and effectiveness. Radiotherapy using the iodine nanoparticle or encapsulated iodine particle exposes and creates more cancer-specific antigens when cells are killed by the radiation, thus better stimulating the immune system.

Some of the iodine nanoparticles described herein unexpectedly exhibited strong visible fluorescence (see Examples 8 and 9). These might be used as probes for microscopy or in vivo to delineate tumors and other structures.

The iodine nanoparticle or encapsulated iodine particle can be optionally imaged or detected by fluorescent x-rays emitted after bombardment with an X-ray beam. This provides an image modality distinct from X-ray absorption and attenuation of a beam. The iodine nanoparticle or encapsulated iodine particle can be localized to a target by various means including vascular leakage, a property of tumors and tissue damage, or attaching a targeting moiety such as an antibody, antibody fragment, protein, peptide, nucleic acid, carbohydrate, drug, or any compound that has affinity to the target. The imaging can also be used in a straightforward detection mode, in vivo or ex-vivo, to qualitatively or quantitatively detect a material.

Figures 7A, 7B:
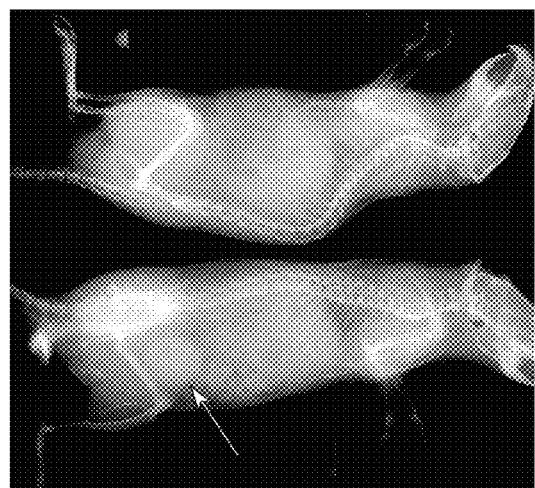
FIG. 7A and FIG. 7B show planar x-ray images of mice after an intravenous injection of the polymer prepared in Example 1.

In one embodiment, the iodine nanoparticle or encapsulated iodine particle may be used for the imaging of the urinary system (see FIG. 7).

Toxicity

The current state of x-ray radiography with iodine-based contrast agents suffers from several important inadequacies. Commercially available contrast agents cause adverse reactions in many patients, including those with allergies, asthma, kidney diseases, and diabetes. These reactions can be severe or fatal. For a person with kidney disease, injection of commercially available iodine agents needed for heart stenting or correcting vascular blockages in the leg and elsewhere can permanently damage the kidneys and the patient will have to go on dialysis the rest of their lives. If a heart attack is imminent, the interventional cardiologist treating a patient that also has weak but functioning kidneys must make the choice of stenting to correct the heart problem and permanently destroying the patient's kidneys or not stenting and risk heart failure. Another deficiency with respect to toxicity of commercially available imaging agents is none are safely available for persons with kidney diseases.

The iodine nanoparticle or encapsulated iodine particle described herein may be size selected to pass through the kidneys. Because of its biocompatible aspect, it may be used in patients with poorly functioning kidneys. This would greatly help in the diagnosis of kidney failure, enabling the proper corrective treatment to be applied before any additional kidney injury occurs.

Figure 3:
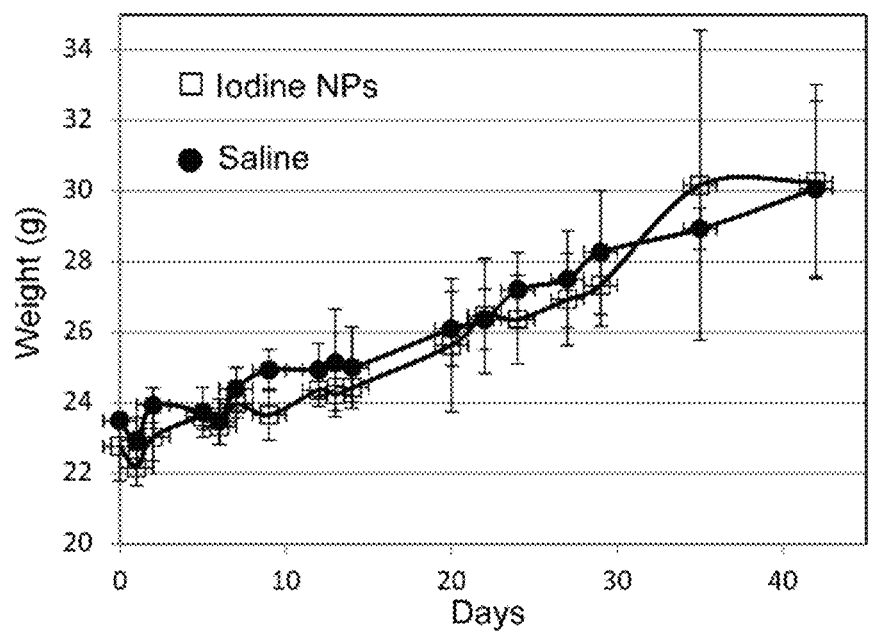
FIG. 3 shows a comparison of the weights of mice after the polymer prepared in Example 1 was injected intravenously to provide an effective dose of 4 g iodine/kg ("Iodine NPs"); and weights of control mice injected intravenously with saline ("Saline"). The graph shows that both groups of mice indistinguishably gained weight over 40 days.

Some of the preparations described have been tested in animals and show no signs of toxicity after an intravenous injection of 4 grams of iodine per kg body weight (see Example 26 and FIG. 3). They gained weight similar to age-matched controls. This is a higher level of injection than any other iodine nanoparticle larger than 5 nm and is a surprising finding.

Some of the preparations described become viscous when highly concentrated and are more easily handled diluted. In order to reach the tested intravenous administration of 4 g iodine/kg level, some preparations were intravenously injected at 100 mg iodine/mL requiring an injection volume of 0.8 mL for a 20 g mouse. This was administered in two doses spaced 3 hours apart. The animals showed no signs of toxicity and gained weight similar to age-matched controls. This is surprising since the whole blood volume of the mouse is about 1.5 mL. Approximately one-half the total blood volume of the animal was injected without significant toxicity, even though the material was quite viscous and greater than 5 nm, thus largely or completely avoiding kidney clearance and designed for extended blood half-life.

In one embodiment, the iodine nanoparticle or the encapsulated iodine particle described herein is biodegradable. In the one embodiment, the iodine nanoparticle or the encapsulated iodine particle is injected into a subject. When the iodine nanoparticle or the encapsulated iodine particle is present in the body, the iodine nanoparticle or encapsulated iodine particle undergoes catabolism. Since this occurs slowly, the actual concentration of iodine nanoparticle or the encapsulated iodine particle breakdown products presented to the subject are at a low concentrations. Thus in one embodiment the iodine nanoparticle or encapsulated iodine particle described herein is less toxic than commercially available iodine contrast agents.

Extended Blood Half-Life Useful for Imaging

An extended blood half-life contrast agent is needed for diagnostic imaging as well as therapy. For example, aneurisms in the brain and dorsal aorta are difficult to detect, but a vascular contrast agent would make this straightforward. The condition of the coronary arteries could be assessed non-invasively, thus preventing many heart attacks, the number one cause of death. The method disclosed herein would address this need and could impact the number of heart attack deaths.

The iodine nanoparticle or encapsulated iodine particle described herein can be size controlled, composition, and coating controlled. These parameters can be used to control the blood half-life, route of body clearance, rate of body clearance, biodistribution, pharmacokinetics, pharmacodynamics, and toxicity profile. This enables such applications as tumor imaging, heart imaging, vascular imaging, and organ imaging.

Many other vascular diseases could be better assessed by the iodine nanoparticle or encapsulated iodine particle described herein including: dorsal aorta aneurism, brain aneurism, arteriovenous malformations, deep vein thrombosis, claudication, renal artery stenosis, peripheral artery disease, Buerger's disease, and intravascular coagulation.

Enhancing Images

One aspect described herein is a method of using the iodine nanoparticle or encapsulated iodine particle for treating cancer by administering the iodine nanoparticle or encapsulated iodine particle which accumulates in the tumor by any mechanism, waiting a time for the tumor-to-local non-tumor concentration ratio to be favorable (greater than 2) and applying radiation. As an example, X-rays may be used that are absorbed by the iodine nanoparticle or encapsulated iodine particle and which results in electrons and other products being emitted by the iodine which can then create free radicals and ionizations or other events that lead to tumor damage.

Cancers treated by this method may include acute lymphoblastic leukemia, acute myeloid leukemia, cancer in adolescents, adrenocortical carcinoma, AIDS-related cancers, AIDS-related lymphoma, anal cancer, astrocytomas, atypical teratoid/rhabdoid tumor, basal cell carcinoma, bile duct cancer, bladder cancer, bone cancer, brain and spinal cord tumors, brain stem glioma, brain tumor, breast cancer, bronchial tumors, Burkitt Lymphoma, carcinoid tumor, carcinoma of unknown primary, cardiac tumors, central nervous system embryonal tumors, central nervous system germ cell tumors, cervical cancer, childhood cancers, cholangiocarcinoma, chordoma, chronic lymphocytic leukemia, chronic myelogenous leukemia, chronic myeloproliferative neoplasms, colon cancer, colorectal cancer, craniopharyngioma, cutaneous T-cell lymphoma, ductal carcinoma in situ, embryonal tumors, endometrial cancer, ependymoma, esophageal cancer, esthesioneuroblastoma, Ewing Sarcoma family of tumors, extracranial germ cell tumor, extragonadal germ cell tumor, eye cancer, fallopian tube cancer, fibrous histiocytoma of bone, osteosarcoma, gallbladder cancer, gastric cancer, gastrointestinal carcinoid tumor, castrointestinal stromal tumors, germ cell tumor, gestational trophoblastic disease, glioma and brain tumor, Hairy Cell leukemia, head and neck cancer, heart cancer, hepatocellular cancer, histiocytosis, Langerhans Cell, Hodgkin Lymphoma, hypopharyngeal cancer, intraocular melanoma, Islet Cell tumors, pancreatic neuroendocrine tumors, Kaposi sarcoma, Langerhans cell histiocytosis, laryngeal cancer, leukemia, lip and oral cavity cancer, liver cancer (primary), low malignant potential tumor, lung cancer, lymphoma, primary macroglobulinemia, Waldenström, male breast cancer, melanoma, Merkel cell carcinoma, mesothelioma, mouth cancer, multiple endocrine neoplasia syndromes, multiple myeloma/plasma cell neoplasm, mycosis fungoides, myelodysplastic syndromes, myelodysplastic/myeloproliferative neoplasms, myeloma, multiple myeloproliferative neoplasms, nasal cavity and paranasal sinus cancer, nasopharyngeal cancer, neuroblastoma, non-Hodgkin lymphoma, non-melanoma, non-small cell lung cancer, oral cavity cancer, oropharyngeal cancer, ovarian cancer, pancreatic cancer, pancreatic neuroendocrine tumors (Islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm/multiple myeloma, pleuropulmonary, blastoma, pregnancy and breast cancer, primary central nervous system lymphoma, primary peritoneal cancer, prostate cancer, rectal cancer, renal cell cancer, transitional cell cancer, retinoblastoma, rhabdomyosarcoma, salivary gland cancer, sarcoma, Sézary syndrome, small cell lung cancer, small intestine cancer, squamous cell carcinoma, squamous neck cancer, stomach cancer, T-cell lymphoma, testicular cancer, throat cancer, thymoma and thymic carcinoma, thyroid cancer, unknown primary carcinomas, urethral cancer, uterine cancer, endometrial, uterine sarcoma, vaginal cancer, vulvar cancer, Waldenström Macroglobulinemia, Wilms Tumor and other kidney tumors.

Software Module or Hardware Module for Enhanced Imaging

One aspect described herein are methods to improve iodine nanoparticle imaging. There are two major modules that can be used separately, but in some cases greatly benefitted by their combined use. The first module comprises tracking software that removes or greatly reduces motion in the real-time acquisition. An alternative to this is gating the input so that the same position in a repetitive sequence is acquired. However, gating in its simplest form is less efficient since useful data during the non-gated time may be discarded. Tracking may be used, for example, to remove or reduce the motion caused by breathing and/or heart beating. The second module is image averaging, where the data is combined over time to reduce the noise and permit increased contrast, i.e., better detection. Minor modules or operations can be included to enhance the imaging, including, but not limited to: binning, edge enhancement/detection, Gaussian and other filters, unsharp masking, brightness and contrast adjustment, thresholding, and sharpening.

A problem exists with standardly used coronary or carotid angiography using standardly available iodine contrast agents. Here, a catheter is inserted, usually in the femoral artery, but sometimes in the radial artery, and it is guided to the hilus of a major coronary artery (right coronary artery, left coronary artery or its two branches, the circumflex artery and the left anterior descending artery), or proximal to the carotid artery entering the neck. The standard iodine agent is injected from the catheter and visualized by fluoroscopy on a TV monitor. The iodine agent is dense enough (about 300-400 mg iodine/cc) to visualize the artery and any blockage or stenosis that may be there. Although the imaging is brief from the iodine injection, it is usually adequate for the purposes of diagnosis, clot removal, stent deployment, balloon angioplasty, or other procedures. The interventional cardiologist can easily follow the angiogram by eye since the heart beats about once per second, and no specialized software is required. A significant problem in these procedures is that patients with kidney disease, poor glomerular filtration, diabetes, or other conditions resulting in compromised kidney function, may have their kidneys completely destroyed for life, necessitating dialysis for the rest of their lives, due to the rapid accumulation of the iodine agent in the kidneys and its severe toxicity when not rapidly eliminated as with normally functioning kidneys.

Figure 12:
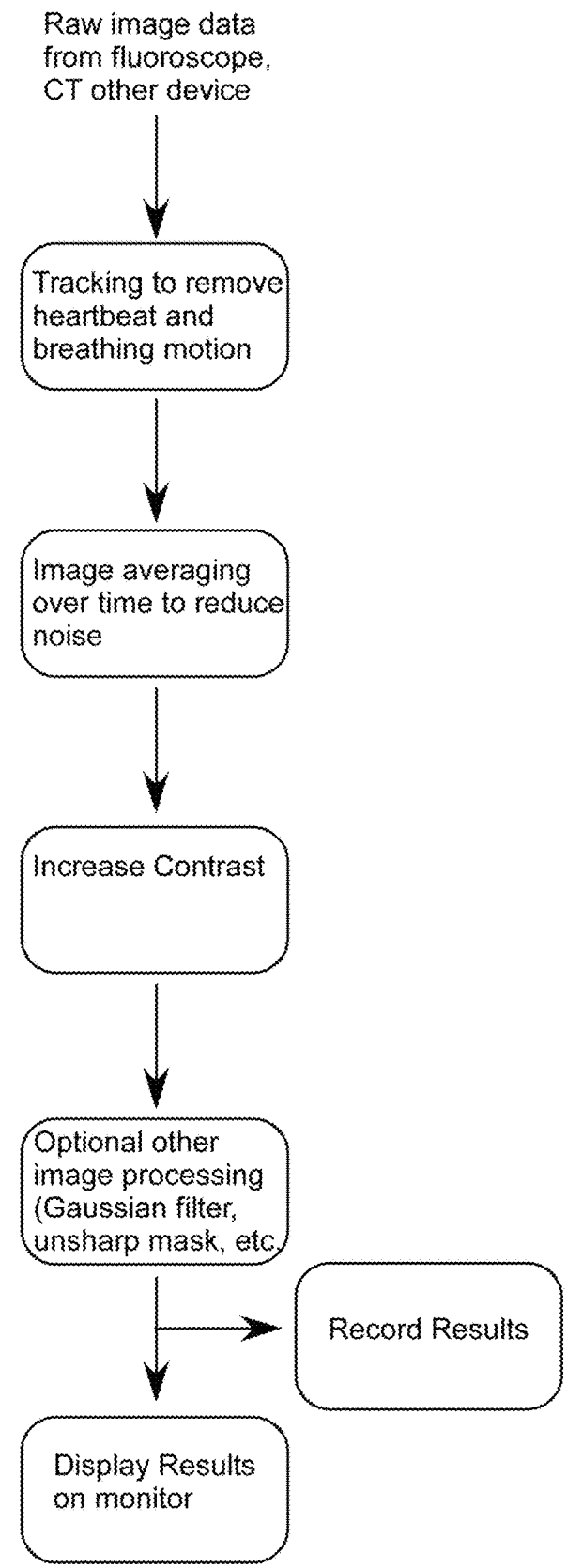
FIG. 12 is a flow diagram of processing software or hardware which enhances iodine nanoparticle images.

In some embodiments, the iodine nanoparticle or encapsulated iodine particle is used in an angiography. The iodine nanoparticle or encapsulated iodine particle can have a size greater than about 5 nm and avoid filtration into the kidneys, thus protecting them. In some embodiments the iodine nanoparticle or encapsulated iodine particle has a concentration lower than commercially available contrast agents, for example, about 100 mg iodine/cc. In some embodiments the software disclosed is used to rapidly a) track the heart beat and breathing motion, thus stabilizing the image, and b) image average over time to reduce noise and boost contrast to an acceptable level. Other imaging process, can also be employed, the end result being that iodine nanoparticles could be used in angiographic procedures. This could spare the kidneys of many patients. A block diagram of this computer program is shown in FIG. 12

Migrating Glioma Cells

Iodine nanoparticles can increase local dose of iodine to tumors. Standard iodine contrast media have been tried in animals and in a clinical trial, but found to have too short a blood half-life for adequate tumor uptake and tumor:non-tumor ratios. To overcome these drawbacks the iodine nanoparticle or encapsulated iodine particle described herein can be used. The iodine nanoparticle or encapsulated iodine particle described herein are nearly colorless, do not color the skin, are organic and can be metabolized, are non-toxic (LD50>4 g Iodine/kg), and are low cost. Preliminary tests showed highly specific localization in gliomas after an intravenous injection.

Figure 11:
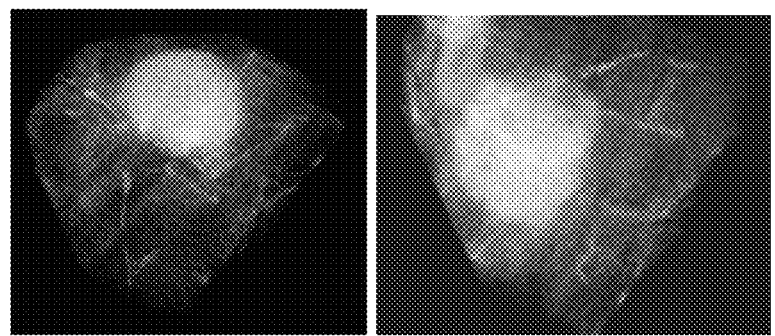
FIG. 11 shows two images demonstrating how iodine leaks out along vessels opened by migrating glioma cells.

As mentioned, one of the biggest problems with treating gliomas are the migrating cells which later cause inevitable recurrence. Surgery, radiotherapy, and chemotherapy cannot fully eradicate these migrating cells. Studies show these migrating cells follow blood vessels. In iodine nanoparticle described herein treated mice with gliomas, spider-like projections of iodine density were found emanating from the tumor (Example 35 and FIG. 11). These result from migrating tumor cells making the blood vessels leaky, allowing the nanoparticles to extravasate. By increasing the radiotherapy volume to include these, the radiation dose will be boosted by the iodine precisely where these migrating tumor cells reside, and provide a way to effectively eradicate them.

Thus in one embodiment is a method for treating migrating glioma cells using the iodine nanoparticle or encapsulated iodine particle described herein.

EXAMPLES

Figure 2:
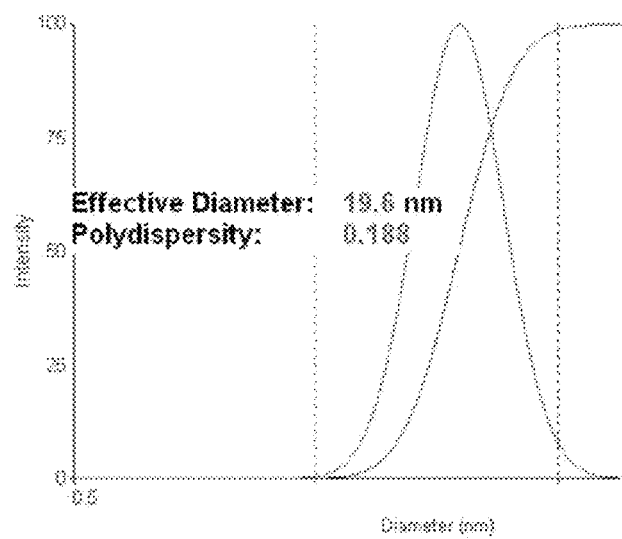
FIG. 2 is a dynamic light scattering graph of the polymer prepared in Example 1. This graph shows that the polymer prepared pursuant to Example 1 has an effective diameter of 19.5 nm and a polydispersity index of 0.188.

Example 1: Preparation of Polymer 172 mg of 5-(N-2,3-Dihydroxypropylacetamido)-2,4,6-triiodo-N,N'-bis(2,3-dihydroxypropyl)isophthalamide was dissolved in 230 μL of water and mixed with 267 mg of sodium metaperiodate dissolved in 1.2 mL of water and reacted in the dark for 30 min. Excess periodate was optionally quenched with a molar excess of ethylene glycol. The product was then dried under vacuum and resuspended in water. 28 mg of carbohydrazide was added and after 10 minutes, 630 mg of 2,000 MW amino-terminated polyethylene glycol. After 16 hours, 79 mg of sodium borohydride was added and reacted for 2.5 hours. The final product was filtered through a 50 KDa ultrafiltration device. The retentate and flow through were both collected. The retentate was washed twice with phosphate buffered saline. Dynamic light scattering showed a diameter of 19.6 nm with a polydispersity index of 0.188 (FIG. 2). Electron microscopy showed dense particles consistent with the dynamic light scattering results (FIG. 1).

Figures 6A, 6B:
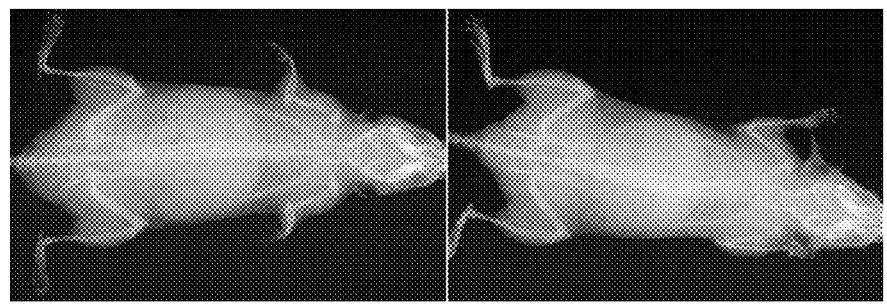
FIG. 6A and FIG. 6B show planar x-ray images of a mouse.

Example 2: In Vivo Imaging Using Polymer 1.6 g Iodine/kg of the >50 kDa polymer of example 1 was intravenously injected into a mouse. Before and 3 min. after injection images were taken using 60 kVp X-rays, shown in FIG. 6. An increase in density was noticeable after injection, especially in the lung region, but also other tissues as well, due to the polymer in the blood perfusing the whole body.

Example 3

The filtrate produced in Example 1 (<50 kDa) was further filtered and washed on a 10 KDa filter and the retentate was intravenously injected into the tail vein of a mouse (600 mg of iodine/kg). No adverse reaction or clinical signs were observed. X-ray imaging after 22 min. revealed substantial accumulation of the contrast agent in the bladder (FIG. 7). This demonstrates a use for urinary system imaging.

Example 4: Scale Up

The preparation of Example 1 was scaled up to produce significantly more polymer. The retentate on a 50 kDa filter was injected in two doses spaced 3 hours apart into mice to achieve a total dose of 4 g iodine per kg body weight. Animals showed this dose was well-tolerated and behaved normally (FIG. 3).

Example 5

43 mg 5-(N-2,3-Dihydroxypropylacetamido)-2,4,6-triiodo-N,N'-bis(2,3-dihydroxypropyl)isophthalamide was dissolved in 60 μL of water and mixed with 80 mg of sodium metaperiodate dissolved in 0.4 mL of water and reacted in the dark for 30 min. Excess periodate was quenched with a molar excess of ethylene glycol. The product was then dried under vacuum and resuspended in water. The pH was adjusted to 12 with sodium hydroxide. After 3 hours, 160 mg of 2,000 MW amino-terminated polyethylene glycol was added. After 16 hours, the product was filtered through a 50 KDa ultrafiltration device. The retentate was washed twice with phosphate buffered saline. Dynamic light scattering showed a diameter of 30.9 nm with a polydispersity index of 0.175.

Example 6

26 mg of 2,3,5-Triiodobenzoic acid was dissolved in 0.50 mL of methanol. 5 mL of cylclohexane was added, then 0.10 mL of Triton X-100. The resultant mixture was then sonicated. The sample was heated to 80° C. for 30 min. 0.02 mL of Triton X-114 was added and the sample slowly added into 8 mL of water while mixing, then sonicated. After 24 hours the sample was filtered with a 0.45 micron filter and dynamic light scattering indicated nanoparticles that were 201 nm in size with a polydispersity index of 0.36.

Example 7

43 mg 5-(N-2,3-Dihydroxypropylacetamido)-2,4,6-triiodo-N,N'-bis(2,3-dihydroxypropyl)isophthalamide was dissolved in 60 μL of water and mixed with 80 mg of sodium metaperiodate dissolved in 0.4 mL of water and reacted in the dark for 30 min. Excess periodate was quenched with a molar excess of ethylene glycol. The product was then dried under vacuum and resuspended in water. 8 mg of adipic acid dihydrazide was added followed by 79 mg of 1,000 MW amino-terminated PEG. After 24 hours, the product was isolated using a 50 KDa filter and washed with phosphate buffered saline. The polymer was concentrated to 150 mg Iodine/mL.

Example 8

11 mg 5-(N-2,3-Dihydroxypropylacetamido)-2,4,6-triiodo-N,N'-bis(2,3-dihydroxypropyl)isophthalamide was dissolved in 0.10 mL of dry dimethyformamide. 8 mg of poly(hexamethylene diisocynaate), viscosity 1,300-2,200 cp, was added and the solution heated to 80° C. for 2 hours. Subsequently, 79 mg of 2,000 MW amino-terminated polyethylene glycol was added. After 16 hours the resulting polymer exhibited a strong yellow-green fluorescence.

Example 9

11 mg 5-(N-2,3-Dihydroxypropylacetamido)-2,4,6-triiodo-N,N'-bis(2,3-dihydroxypropyl)isophthalamide was dissolved in 0.05 mL of dry dimethyformamide. 14 mg of diethylenetriaminepentaacetic dianhydride dissolved in 0.2 mL of dry dimethyformamide was added and the solution heated for 2 hours at 80° C. for 2 hours. 79 mg of 2,000 MW amino-terminated polyethylene glycol was then added. After 16 hours 1.4 mL of water was added. The resultant polymer showed a strong blue fluorescence.

Example 10

11 mg 5-(N-2,3-Dihydroxypropylacetamido)-2,4,6-triiodo-N,N'-bis(2,3-dihydroxypropyl)isophthalamide was dissolved in 0.5 mL of 1.5 M sodium hydroxide. 4 microliters of epichlorohydrin was added and the solution heated at 50° C. for 16 hours. 1 mL of water was added and the resulting polymer was isolated using a 50 kDa filter.

Example 11

11 mg 5-(N-2,3-Dihydroxypropylacetamido)-2,4,6-triiodo-N,N'-bis(2,3-dihydroxypropyl)isophthalamide was dissolved in 0.1 mL of dry dimethyformamide and reacted with a molar amount of diglycidyl ether, 1,4 butandiodiglycidylether, or poly(ethylene glycol) diglycidyl ether for 24 hours. 79 mg of 2,000 MW amino-terminated polyethylene glycol was then added. After 16 hours 1.4 mL of water was added. The resulting polymers were isolated using a 50 kDa filter.

Example 12

43 mg 5-(N-2,3-Dihydroxypropylacetamido)-2,4,6-triiodo-N,N'-bis(2,3-dihydroxypropyl)isophthalamide was dissolved in 60 μL of water and mixed with 80 mg of sodium metaperiodate dissolved in 0.4 mL of water and reacted in the dark for 30 min. Excess periodate was quenched with a molar excess of ethylene glycol. The product was then dried under vacuum and resuspended in water. This was reacted with 10 mg of NH2-(PEG)4-NH2 for 24 hours. The resulting iodine polymers were isolated using a 50 kDa filter.

Example 13: Preparation of Encapsulated Iodine Particle 22 mg 5-(N-2,3-Dihydroxypropylacetamido)-2,4,6-triiodo-N,N'-bis(2,3-dihydroxypropyl)isophthalamide was dissolved in 30 μL of water and mixed with 40 mg of sodium metaperiodate dissolved in 0.2 mL of water and reacted in the dark for 30 min. Excess periodate was quenched with a molar excess of ethylene glycol. The product was then dried under vacuum and resuspended in 2 mL of methanol and spun at 3 krpm for 5 min. The supernatant was then reacted with 15 mg dodecylamine with 17 mg sodium triacetoxyborohydride for 3 hours. The solution was rotary evaporated to dryness and redissolved in 0.3 mL of cyclohexane. This was added to 2 mL of water with 0.05 mL of Tween 80 and sonicated to form an emulsion. The cyclohexane was then removed by heating at 90° C. for 1 hour, reducing the size of the encapsulated iodine particles. Dynamic light scattering indicated an average hydrodynamic size of 343 nm with a polydispersity index of 0.41.

Example 14

38 mg 5-(N-2,3-Dihydroxypropylacetamido)-2,4,6-triiodo-N,N'-bis(2,3-dihydroxypropyl)isophthalamide was dissolved in 30 μL of water and mixed with 0.09 mL of 8% glutaraldehyde (in water). 0.06 mL of concentrated hydrochloric acid was added and the solution rotary evaporated at 40° C., then resuspended in water. Micron to mm-sized iodine encapsulated iodine particles were formed.

Example 15

11 mg 5-(N-2,3-Dihydroxypropylacetamido)-2,4,6-triiodo-N,N'-bis(2,3-dihydroxypropyl)isophthalamide was dissolved in 0.015 mL of water. 2 mg of gluataraldehyde in 0.025 mL and 0.005 mL of concentrated hydrochloric acid were added. This solution was then added to 0.5 mL xylene containing 113 mg sodium dodecyl sulfate, sonicated, and rotary evaporated at 50° C. To the material was added 1 mL dichloromethane containing 0.05 mg 2,000 MW amino-PEG. Sonication formed a stable emulsion. After 1 hour 0.4 mL water was added and the solution rotary evaporated at 50° C. to 0.2 mL. Light microscopy revealed nanoparticles 0.5 to 2 microns in diameter.

Example 16

5-(N-2,3-Dihydroxypropylacetamido)-2,4,6-triiodo-N,N'-bis(2,3-dihydroxypropyl)isophthalamide was dissolved in water and mixed with 1.2 molar excess of sodium metaperiodate and reacted in the dark for 30 min. The product was then dried under vacuum and resuspended in methanol and spun at 3 krpm for 5 min. The supernatant was reacted with 1.5 molar excess (to the iodine compound) of either: a) carbohydrazide, b) ethylenediamine, c) polyethyleneamine. A 1.5 molar excess of sodium triacetoxyborohydride was added and reacted for 24 hours. Subsequently, the samples were dried, dissolved in dichloromethane, and added to a 10-fold volume excess of water containing the biodegradable surfactant polycaprolactone-PEG and sonicated. Nanoparticles were concentrated and purified on a 50 kDa molecular centrifugal filter.

Example 17

2,3,5-Triiodobenzoic acid was dissolved dry dimethylformamide. It was reacted with ethylenediamine using 1-ethyl-3-(3-dimethylaminopropyl)carbodiimide as a crosslinking agent to form triiodobenzoic acid dimers. These were hydrophobic. The reaction was vacuum dried and the product suspended in hexane. An emulsion was formed using 1 mL of the hexane dissolved product mixed with 10 mL of water containing 10 microliters of polysorbate 80 upon sonication. The hexane was removed by heating at 80° C. for 1 hour, resulting in smaller nanoparticles. These were then concentrated using a 50 kDa centrifugal filter followed by washing in phosphate buffered saline.

Example 18

5-(N-2,3-Dihydroxypropylacetamido)-2,4,6-triiodo-N,N'-bis(2,3-dihydroxypropyl)isophthalamide was dissolved in dry dimethylformamide and reacted with a 0.3 molar amount of 1,1'-carbonyldiimidazole. The polymers produced were added to a 10-fold volume excess of water containing the biodegradable surfactant polycaprolactone-PEG and sonicated. Iodine encapsulated iodine particles were concentrated and purified on a 50 kDa molecular centrifugal filter. This produced encapsulated iodine particles with both a core and shell that were biodegradable. The core material, linked by ester bonds, then reverts upon hydrolysis to the original 5-(N-2,3-Dihydroxypropylacetamido)-2,4,6-triiodo-N,N'-bis(2,3-dihydroxypropyl)isophthalamide compound which is FDA approved and has an intravenous LD50 value of 24.2 g iodine/kg in mice. This refers to an acute dose, but since the encapsulated iodine particle will degrade slowly it will present a lower concentration to the body, thus making it even less toxic.

Example 19

3 mg 5-(N-2,3-Dihydroxypropylacetamido)-2,4,6-triiodo-N,N'-bis(2,3-dihydroxypropyl)isophthalamide was dissolved in 0.1 mL dry dimethylsulfoxide. 92 mg of polyethylene glycol (3400 MW) was added along with 87 mg 1,1'-carbonyldiimidazole. After 1 hour, 1 mL of water was added and the product was put through a high pressure homogenizer at 30 kpsi until a nearly clear solution was obtained. This was then 0.2 micrometer filtered and the nanoparticles collected, washed and concentrated on a 50 kDa centrifugal filter.

Example 20

Liposome preparation: 2 microliters of poly(ethylene glycol) diglycidyl ether (500 MW) was diluted in 1 mL of water. 25 microliters of this solution was added to 20 mg 5-(N-2,3-Dihydroxypropylacetamido)-2,4,6-triiodo-N,N'-bis(2,3-dihydroxypropyl)isophthalamide with 1 microliter of 1 Normal sodium hydroxide and incubated for 1 hour (solution 1). In another container, 200 mg lecithin was dissolved in 0.2 mL of dichloromethane and added to 10 mL of mineral oil (solution 2). Solution 1 was injected through a 28 gauge needle into solution 2, and homogenized using a rotating blade homogenizer. The product was then further dispersed into smaller particles using a high pressure homogenizer operating at 30 kpsi. The product was centrifuged at 3 kg and the pellet washed 2 times with hexane. 2 mL of water was added to the pellet, the sample sonicated, and heated to 80 degrees C. to remove remaining hexane. The product was filtered through a 0.2 micron filter, then concentrated and purified further on a 50 kDa molecular centrifugal filter.

Example 21: Crosslinking to a Shell Component 6 mg 5-(N-2,3-Dihydroxypropylacetamido)-2,4,6-triiodo-N,N'-bis(2,3-dihydroxypropyl)isophthalamide was mixed in 10 microliters of water with 3 microliters of 8% glutaraldehyde. This was mixed with 0.5 mL of toluene containing 5 mg of oleic acid. This was sonicated to form an emulsion and reacted for 1 hour. The precipitate formed was washed with hexane and the final product dispersed in water using Brij S100 surfactant.

Example 22: Silane Coating 17 mg 5-(N-2,3-Dihydroxypropylacetamido)-2,4,6-triiodo-N,N'-bis(2,3-dihydroxypropyl)isophthalamide or iodobenzene polymers in 0.05 mL of water was mixed with a solution made of 5 microliters of trichloro(octadecyl)silane, 200 microliters of dichloromethane and 1 mL of mineral oil. The mixture was sonicated. In some preparations, NaOH was mixed in the water phase to enhance silane polymerization. The emulsion was then centrifuged and washed with hexane. Finally, the pellet was dissolved in 0.5 mL of water with 10 microliters of Brij 100 as surfactant.

Example 23

5-Amino-2,4,6-triiodoisophthalic acid was dissolved in water and mixed with a 0.5 molar amount of ethylenediamine hydrochloride. The water soluble crosslinker 1-ethyl-3-(3-dimethylaminopropyl)carbodiimide in equimolar amount was used to form the polymer.

Example 24

3 mg 5-Amino-2,4,6-triiodoisophthalic acid was mixed with 7 mg 1,1-carbonyldiimidazole as dry chemicals and ground with a pestle. After reacting, 0.7 mg polyethyleneamine (MW 800) was added and also ground for reaction. The product was recovered in 2 mL of water and purified on centrifugal filters.

Example 25

8 mg 5-Amino-2,4,6-triiodoisophthalic acid was mixed with 5.5 mg 1,1'-carbonyldiimidazole and ground with a pestle. After reacting, 56 mg of amino-PEG was added along with 0.5 microliters of concentrated hydrochloric acid. After 4 hours, 1 mL of water was added and the product purified on a centrifugal filter.

Example 26: Toxicity Testing

Three outbred CD1 mice were dosed at 4 g Iodine/kg, administered via tail vein in 2 equal doses 3 hours apart. An age-matched control group was injected with the same volume of saline. Mice were weighed regularly the two groups showed no significant differences (FIG. 3). Weight gain was normal.

Example 27: Toxicity Testing

This toxicity test involved the metabolic effects as measured by blood analysis of serum clinical chemistry analytes and hematocrits. Three outbred CD1 mice were dosed at 4 g Iodine/kg of the polymer of Example 1, administered via tail vein in 2 equal doses 3 hours apart. An age-matched control group was injected with the same volume of saline. After one month, blood samples were taken and analyzed. Results are given in Table 1. Surprisingly, no toxicity was detected and the iodine polymer group was indistinguishable from the control group.

TABLE 1

| | GROUP | | | | | | | |
| --- | --- | --- | --- | --- | --- | --- | --- | --- |
| | SALINE | | | | POLYMER FROM EXAMPLE 1 | | | |
| Patient | 1 | 8 | 10 | mean | 2 | 4 | 5 | mean |
| ALP | 79 | 121 | 133 | 111 | 49 | 60 | 94 | 67.67 |
| ALT | 18 | 28 | 28 | 24.7 | 27 | 19 | 14 | 20 |
| AST | 58 | 105 | 71 | 78 | 133 | 51 | 47 | 77 |

TABLE 1-continued

| | GROUP | | | | | | | |
|---|---|---|---|---|---|---|---|---|
| | SALINE | | | | POLYMER FROM EXAMPLE 1 | | | |
| Patient | 1 | 8 | 10 | mean | 2 | 4 | 5 | mean |
| Creatine Kinase | 149 | 384 | 217 | 250 | 608 | 127 | 109 | 281.33 |
| GGT | 1 | 1 | 1 | 1 | 1 | 1 | 1 | 1 |
| Albumin | 2.8 | 2.4 | 2.7 | 2.63 | 2.9 | 2.6 | 2.6 | 2.7 |
| Total Protein | 5 | 4.4 | 5 | 4.8 | 5.1 | 4.6 | 4.8 | 4.83 |
| Globulin | 2.2 | 2 | 2.3 | 2.17 | 2.2 | 2 | 2.2 | 2.13 |
| Total Bilirubin | 0.1 | 0.1 | 0.1 | 0.1 | 0.1 | 0.1 | 0.1 | 0.1 |
| Bulirubin - Conj | <0.1 | <0.1 | <0.1 | <0.1 | <0.1 | <0.1 | <0.1 | <0.1 |
| BUN | 12 | 25 | 24 | 20.3 | 18 | 6 | 18 | 14 |
| Creatinine | <0.1 | 0.1 | 0.1 | 0.1 | 0.1 | <0.1 | <0.1 | 0.1 |
| Cholesterol | 108 | 100 | 126 | 111 | 105 | 111 | 95 | 103.67 |
| Glucose | 217 | 239 | 255 | 237 | 223 | 215 | 271 | 236.33 |
| Calcium | 8.3 | 8.3 | 8.7 | 8.43 | 9.2 | 8.8 | 8.5 | 8.83 |
| Phosphorus | 6.5 | 4.4 | 6.4 | 5.77 | 6.8 | 6.2 | 4.5 | 5.83 |
| TCO2 (Bicarbonate) | 17 | 18 | 18 | 17.7 | 16 | 19 | 18 | 17.67 |
| Chloride | 112 | 112 | 112 | 112 | 110 | 13 | 113 | 78.67 |
| Potassium | 5.9 | 4.7 | 5.2 | 5.27 | 4.8 | 4.9 | 4.8 | 4.83 |
| Sodium | 144 | 144 | 143 | 144 | 144 | 146 | 144 | 144.67 |
| ALB/GLOB Ratio | 1.3 | 1.2 | 1.2 | 1.23 | 1.3 | 1.3 | 1.2 | 1.27 |
| BUN/Creatinine Ratio | 120 | 250 | 240 | 203 | 180 | 160 | 180 | 173.33 |
| Bilirubin - Unconj. | 0 | 0 | 0 | 0 | 0 | 0 | 0 | 0 |
| NA/K Ratio | 24 | 31 | 28 | 27.7 | 30 | 30 | 30 | 30 |
| Anion Gap | 21 | 19 | 18 | 19.3 | 23 | 19 | 18 | 20 |
| SDMA | 5 | 7 | 6 | 6 | 5 | 7 | 5 | 5.67 |
| WBC | 6 | 3.5 | 3.1 | 4.2 | 4.5 | 2.9 | 2.4 | 3.27 |
| RBC | 8.56 | 8.12 | 7.38 | 8.02 | 8.92 | 7.27 | 8.36 | 8.18 |
| HGB | 13.6 | 11.9 | 11.4 | 12.3 | 13.1 | 11.4 | 11.9 | 12.13 |
| HCT | 41.8 | 38.3 | 37 | 39 | 41.9 | 35.5 | 39.1 | 38.83 |
| MCV | 49 | 47 | 50 | 48.7 | 47 | 49 | 47 | 47.67 |
| MCH | 15.9 | 14.7 | 15.4 | 15.3 | 14 | 15.7 | 14.2 | 14.63 |
| MCHC | 32.5 | 31.1 | 30.8 | 31.5 | 31.3 | 32.1 | 30.4 | 31.27 |
| % Neutrophil | 10 | 16.4 | 5 | 10.5 | 12.5 | 16 | 13.7 | 14.07 |
| % Lymphocyte | 88 | 68.6 | 93 | 83.2 | 74.7 | 81 | 71.4 | 75.7 |
| % Monocyte | 2 | 2.8 | 0 | 1.6 | 7.3 | 2 | 13.3 | 7.53 |
| % Eosinophil | 0 | 11.6 | 1 | 4.2 | 5.1 | 1 | 0.8 | 2.3 |
| % Basophil | 0 | 0.6 | 1 | 0.53 | 0.4 | 0 | 0.8 | 0.4 |
| Auto Platelet | 1305 | 1311 | 647 | 1308 | 1297 | 180 | 1730 | 1069 |
| Neutrophil | 600 | 574 | 155 | 443 | 563 | 464 | 329 | 452 |
| Lymphocyte | 5280 | 2401 | 2883 | 3521 | 3362 | 2349 | 1714 | 2475 |
| Monocyte | 120 | 98 | 0 | 72.7 | 329 | 58 | 319 | 235.33 |
| Eosinophil | 0 | 406 | 31 | 146 | 229 | 29 | 19 | 92.33 |
| Basophil | 0 | 21 | 31 | 17.3 | 18 | 0 | 19 | 12.33 |
| T3 | 51 | 47 | 57 | 51.7 | 46 | 39 | 49 | 44.67 |
| T4 | 6.8 | 5 | 5.7 | 5.83 | 8.5 | 5 | 7.1 | 6.87 |
| cTSH | 0.03 | 0.05 | 0.04 | 0.04 | 0.04 | 0.04 | 0.04 | 0.04 |

Figure 4:
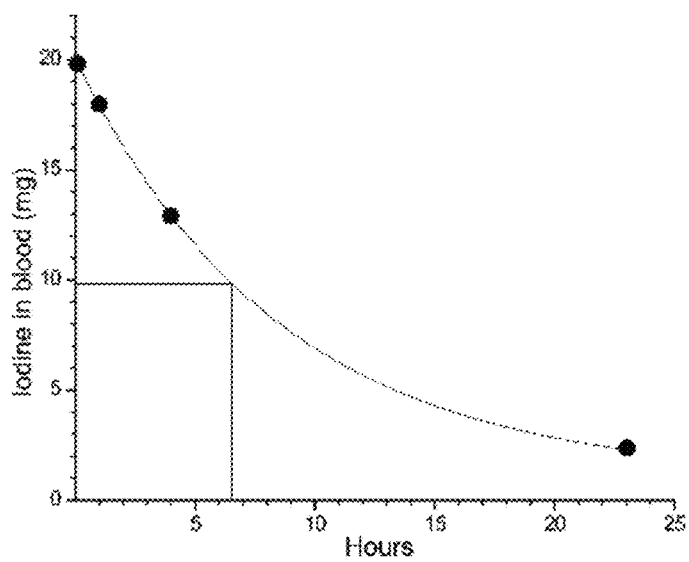
FIG. 4 is a graph showing the blood half-life of the polymer prepared in Example 1.

Example 28: Blood Half-Life of Polymer 20 mg of the iodine nanoparticles of Example 1 were injected IV into mice and blood samples taken at various times thereafter. Blood was allowed to clot, centrifuged, and serum iodine spectrally quantified. The blood half-life was determined to be 6.5 hours (see FIG. 4).

Example 29: Liver Clearance of Polymer

Figure 5:
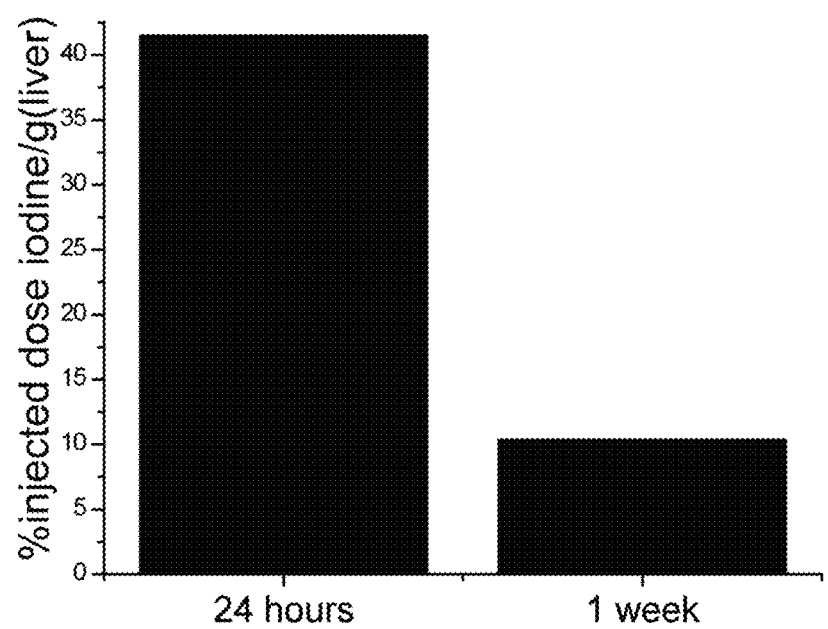
FIG. 5 is a bar graph demonstrating the liver clearance of the polymer prepared in Example 1 over 7 days. Approximately 40% of the injected dose of iodine/g of liver was found in the liver 24 hours after an intravenous injection of the polymer prepared in Example 1 at an effective dose of 1.8 g iodine/kg. Only 10% of the injected dose of iodine/g of liver was still present in the liver after 7 days.

The iodine content of the liver was measured over time. At 24 hours after injection of 1.8 g iodine/kg, 39% of the injected dose of iodine was found in the liver. The liver weight was 0.94 g, calculating to 41.8% of the injected dose/g(liver). Iodine content was then measured 1 week after IV injection and the liver loading dropped to 10.4% id/g. This represents a 75% clearance from the liver in 6 days (see FIG. 5), indicating that these iodine nanoparticles appear to be slowly metabolized and cleared.

Example 30: In Vivo Imaging Using Polymer 1.6 g Iodine/kg of the >50 kDa polymer of example 1 was intravenously injected into a mouse. Before and 3 min. after injection images were taken using 60 kVp X-rays, shown in FIG. 6. An increase in density was noticeable after injection, especially in the lung region, but also other tissues as well, due to the polymer in the blood perfusing the whole body.

Example 31

The filtrate produced in Example 1 (<50 kDa) was further filtered and washed on a 10 KDa filter and the retentate was intravenously injected into the tail vein of a mouse (600 mg of iodine/kg). No adverse reaction or clinical signs were observed. X-ray imaging after 22 min. revealed substantial accumulation of the contrast agent in the bladder (FIG. 7). This demonstrates a use for urinary system imaging.

Example 32: Comparison with Commercially Available Agent (in Kidneys)

Figure 8A:
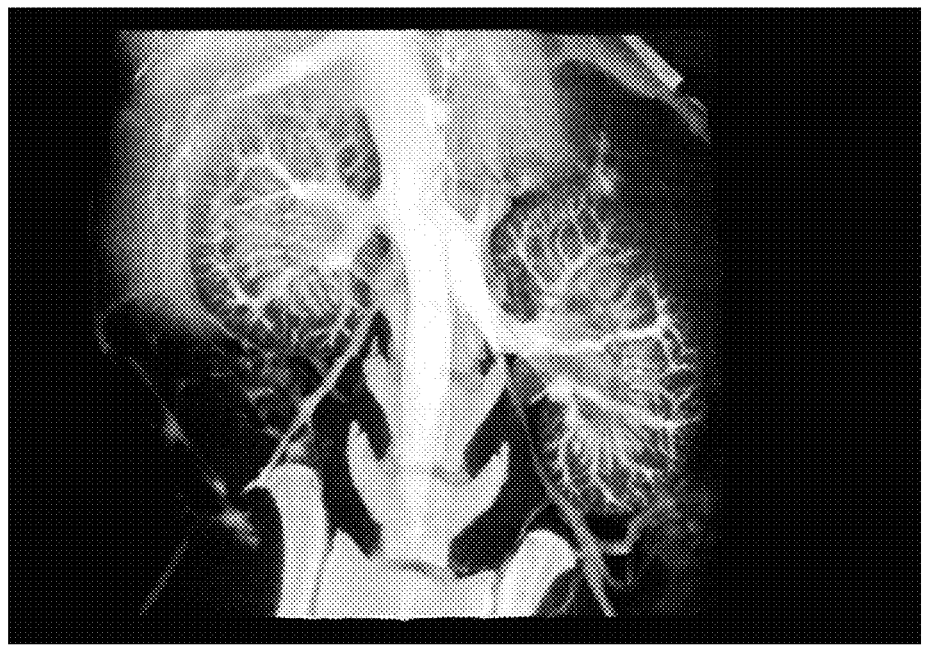
FIG. 8A and FIG. 8B show microCT scans of the kidney region in a mouse.
Figure 8B:
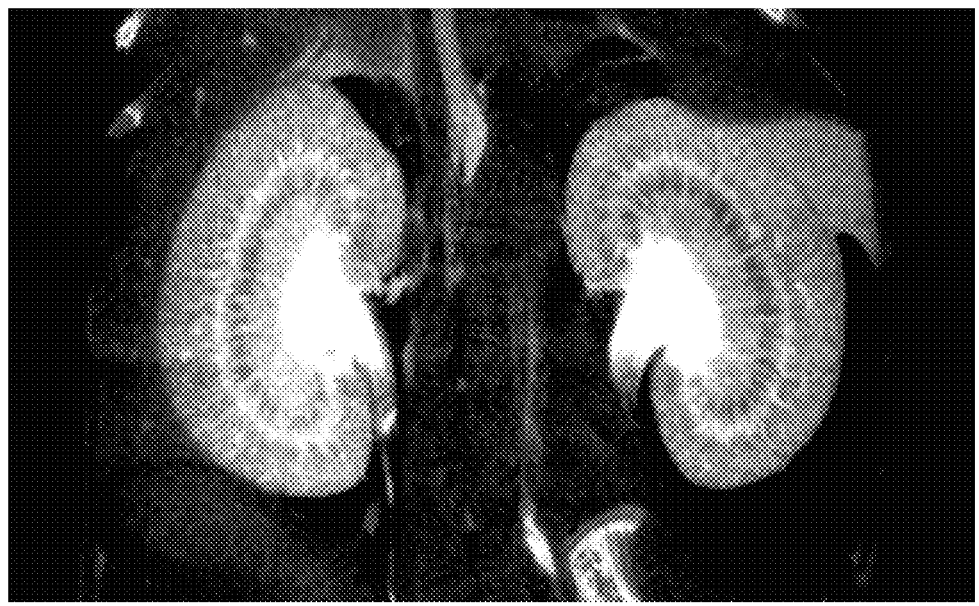

A mouse was injected with the polymer prepared in Example 1 at an effective dose of 1.75 g iodine/kg. FIG. 8(*a*) was obtained two minutes after injection and shows a clear visual of the vascular blood supply to the kidneys of the mouse. A mouse was injected with a standard iodine contrast agent at an effective dose of 2.5 g iodine/kg. FIG. 8(*b*) was obtained two minutes after injection and shows the iodine has rapidly entered the kidneys and is being quickly removed from the blood.

Example 33: Comparison with Commercially Available Agent (in Lung)

Figure 9A:
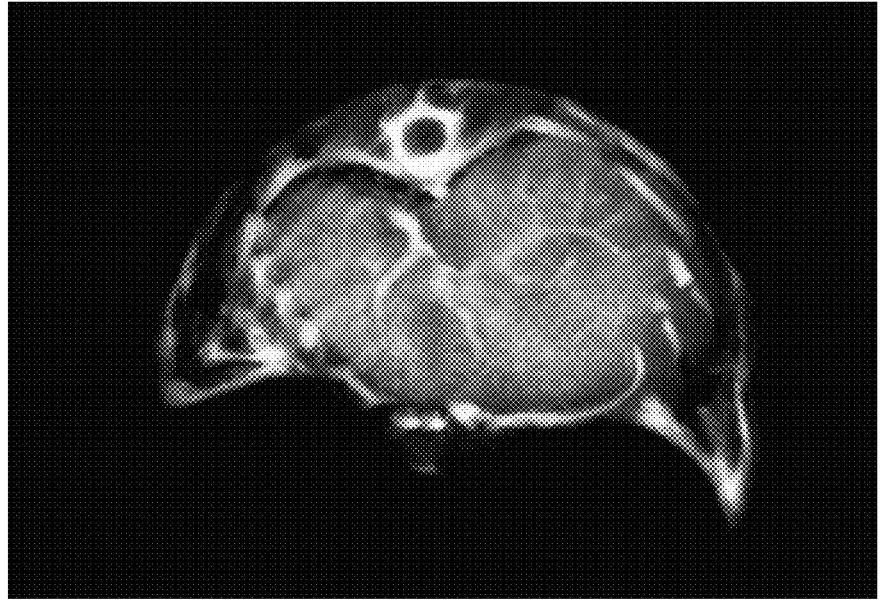
FIG. 9A and FIG. 9B show microCT scans of the lung region in a mouse.
Figure 9B:
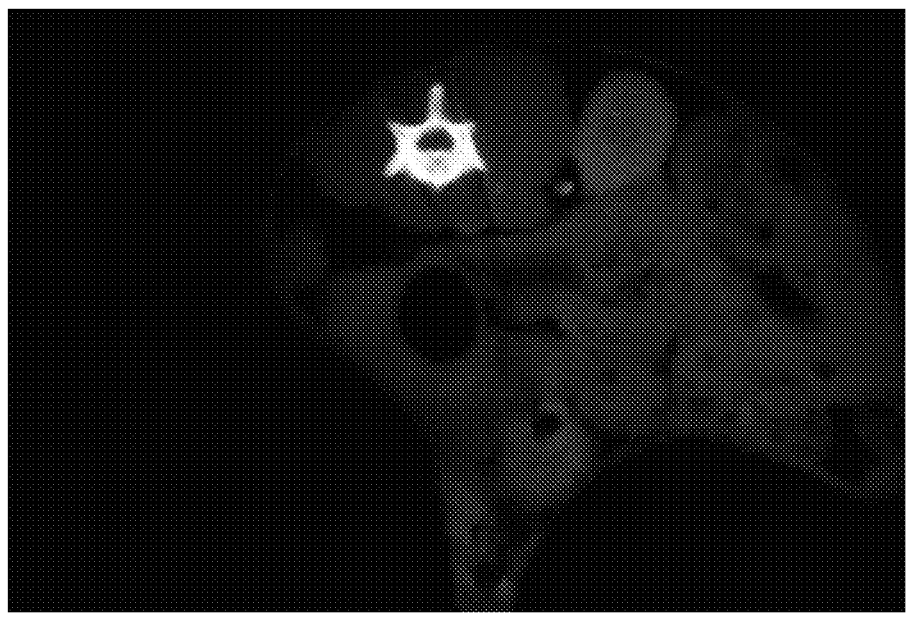

A mouse was injected with the polymer prepared in Example 1 at an effective dose of 1.75 g iodine/kg. FIG. 9(*a*) was obtained 30 minutes after injection and shows a clear visual of the vasculature in the lugs. A mouse was injected with a standard iodine contrast agent at an effective dose of 1.75 g iodine/kg. FIG. 9(*b*) was obtained 30 minutes after injection and shows no clear visualization of any vasculature.

Example 34: Brain Tumor Imaging with Polymer

U87 human glioma brain tumor cells were implanted in nude mouse brains. After growing for 3 weeks, mice were intravenously injected with the polymer of Example 1 at 2.8 g iodine/kg. 24 hours later the mice were imaged by microCT. A representative image is shown in FIG. 10(*a*). Using standards, it was found that the tumor loaded to ~0.6% iodine by weight by 24 hours. 16×16×16 µm3 voxels were averaged so the microscopic iodine concentrations could actually be higher. Some voxels showed as high as 3.4% iodine loading. 0.6% actual concentration is calculated to give a Dose Enhancement Factor (DEF) of 2.1. 3.4% will give a never before achieved in animals DEF of 12.3. After 3 days, the tumor concentration only decremented slightly to 0.5% as shown in FIG. 10(*b*).

Example 35: Migrating Glioma Cells

U87 human glioma brain tumor cells were implanted in nude mouse brains. After growing for 3 weeks, mice were intravenously injected with the polymer of Example 1 at 2.8 g iodine/kg. 24 hours later the mice were imaged by microCT. After computationally removing the skull, tentacle-like strands could be seen emanating from the main tumor mass. Their visibility was caused by a high concentration of the iodine nanoparticles. Gliomas are known to spread by migrating along blood vessels, also making them leaky to nanoparticles. These tentacles are therefore believed to be direct imaging of the migrating glioma cells. Since radiation would be boosted where there is iodine, this surprisingly provides a way, hitherto impossible, to treat and eliminate migrating glioma cells, the current cause of glioma recurrence and invariable death.

Example 36

5-(N-2,3-Dihydroxypropylacetamido)-2,4,6-triiodo-N,N'-bis(2,3-dihydroxypropyl)isophthalamide was dissolved in water and mixed with a 2.1 molar excess of sodium metaperiodate and reacted in the dark for 30 min. The product was then dried under vacuum and resuspended in water. An equal volume of hexane containing a 6 molar excess of dodecylamine was added and reacted for 16 hours with stirring. The product was centrifuged and the upper hexane layer became yellow in color. It was removed and dried by rotary evaporation to a yellow oil. This product was dissolved in tetrahydrofuran containing 10 mg/ml of the surfactant polycapriolactone-polyethylene glycol, and mixed with a 10-fold volume amount of water and sonicated. Core-shell nanoparticles formed that were 260 nm in size.

Example 37

3-Dihydroxypropylacetamido)-2,4,6-triiodo-N,N'-bis(2,3-dihydroxypropyl)isophthalamide was dissolved in water and mixed with a 2.1 molar excess of sodium metaperiodate and reacted in the dark for 30 min. The product was then dried under vacuum and resuspended in water. An equal volume of hexane containing a 6 molar excess of oleylamine was added and reacted for 16 hours with stirring. The product was centrifuged and the upper hexane layer became yellow in color. It was removed and dried by rotary evaporation to a yellow oil. This product was dissolved in tetrahydrofuran containing 10 mg/ml of the surfactant polycapriolactone-polyethylene glycol, and mixed with a 10-fold volume amount of water and sonicated. Core-shell nanoparticles formed that were about 200 nm in size.

Example 38

(Droxypropylacetamido)-2,4,6-triiodo-N,N'-bis(2,3-dihydroxypropyl)isophthalamide was dissolved in water and mixed with a 2.1 molar excess of sodium metaperiodate and reacted in the dark for 30 min. The product was then dried under vacuum and extracted with methanol. A 6-fold excess of octanoic hyrazide was added and reacted for 16 hours. The product was extracted into hexane and dried by rotary evaporation. This material was dissolve in tetrahydrofuran containing 10 mg/ml of the surfactant polycapriolactone-polyethylene glycol, and mixed with a 10-fold volume amount of water and sonicated. Core-shell nanoparticles formed that were about 150 nm in size.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:
1. An iodine nanoparticle which is a reaction product of functionalized triiodobenzene, a linking monomer, and a biocompatible polymer;
   wherein said functionalized triiodobenzene, said linking monomer, and said biocompatible polymer are covalently cross-linked resulting in the structure of said nanoparticle being non-dendritic, non-uniform, and non-linear;
   wherein the reaction product is not a dimer;
   wherein said nanoparticle has sufficient iodine density to be imaged by an imaging device following administration to a subject;
   wherein said nanoparticle provides for an extended blood half-life of at least 6 hours,
   wherein:
     said functionalized triiodobenzene is functionalized 1,3,5-triiodobenzene or functionalized 2,4,6-triiodobenzene,
     said linking monomer is carbohydrazide,
     said biocompatible polymer is polyethyleneglycol-amine, and
   wherein said nanoparticle comprises the structure:

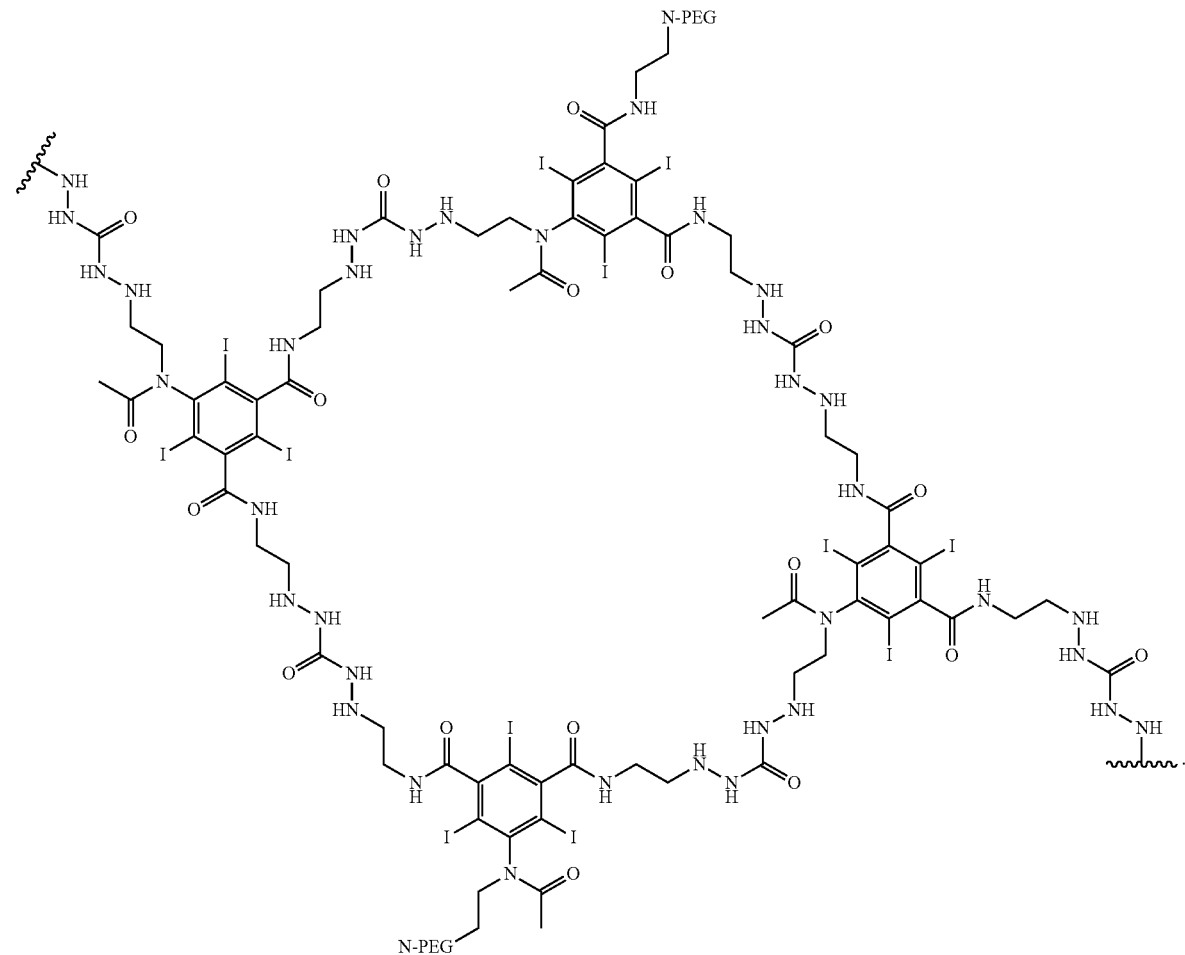

2. The iodine nanoparticle according to claim 1, wherein said nanoparticle has a diameter from about 0.25 μm to about 100 μm.

3. The iodine nanoparticle according to claim 1, wherein said nanoparticle has a diameter from about 1 nm to about 500 nm.

4. A method of producing enhanced imaging by exposing the iodine nanoparticle according to claim 1 to radiation.

* * * * *